United States Patent
Lee et al.

(10) Patent No.: US 11,535,827 B2
(45) Date of Patent: Dec. 27, 2022

(54) PLATED HEPATOCYTES AND PREPARATION AND USES THEREOF

(71) Applicant: LifeNet Health, Virginia Beach, VA (US)

(72) Inventors: Jung Bok Lee, Virginia Beach, VA (US); Angela Murchison, Virginia Beach, VA (US); Edward LeCluyse, Virginia Beach, VA (US); Jingsong Chen, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 416 days.

(21) Appl. No.: 16/649,476

(22) PCT Filed: Sep. 22, 2018

(86) PCT No.: PCT/US2018/052315
§ 371 (c)(1),
(2) Date: Mar. 20, 2020

(87) PCT Pub. No.: WO2019/060790
PCT Pub. Date: Mar. 28, 2019

(65) Prior Publication Data
US 2020/0239839 A1    Jul. 30, 2020

Related U.S. Application Data

(60) Provisional application No. 62/562,127, filed on Sep. 22, 2017.

(51) Int. Cl.
*C12N 5/071*    (2010.01)
*G01N 33/50*    (2006.01)

(52) U.S. Cl.
CPC ......... *C12N 5/067* (2013.01); *G01N 33/5067* (2013.01); *C12N 2502/1323* (2013.01); *C12N 2502/28* (2013.01)

(58) Field of Classification Search
CPC .................................................. C12N 5/067
See application file for complete search history.

(56) References Cited

FOREIGN PATENT DOCUMENTS

| JP | 62285781 A | 12/1987 |
|---|---|---|
| WO | 2008156667 A1 | 12/2008 |

(Continued)

OTHER PUBLICATIONS

International Preliminary Report on Patentability for International Application No. PCT/US2018/052315, dated Mar. 24, 2020, 9 pages.

(Continued)

*Primary Examiner* — Rosanne Kosson
(74) *Attorney, Agent, or Firm* — RatnerPrestia

(57) ABSTRACT

The present invention provides a product comprising plated human hepatocytes on a surface and at least some of the plated hepatocytes are in one or more hepatocyte clusters on feeder cells, which are attached to the surface. A method of preparing plated human hepatocytes is also provided. The preparation method comprises applying human hepatocytes to a surface in the presence of feeder cells, co-culturing the applied hepatocytes with the feeder cells, and forming one or more hepatocyte clusters by the co-cultured hepatocytes on the feeder cells, which are attached to the surface. The plated hepatocytes may be used for various purposes, including the preparation of a hepatitis B virus (HBV) infected hepatocyte culture model and drug testing.

16 Claims, 27 Drawing Sheets

(56) References Cited

FOREIGN PATENT DOCUMENTS

WO      2014143998 A1    9/2014
WO      2017024206 A1    2/2017

OTHER PUBLICATIONS

International Search Report and Written Opinion for International Application No. PCT/US2018/052315, dated Dec. 4, 2018, 11 pages.
Otsuka et al., "Micropatterned co-culture of hepatocyte spheroids layered on non-parenchymal cells to understand heterotypic cellular interactions", Sci. Technol. Adv. Mater., Nov. 13, 2013, 14(6): 1-10, doi:10.1088/1468-6996/14/065003.
Lui et al., "Hepatocyte Cocultures with Endothelial Cells and Fibroblasts on Micropatterned Fibrous Mats to Promote Liver-Specific Functions and Capillary Formation Capabilities" Biomacromolecules, Feb. 18, 2014, 15(3): 1044-1054.
Sasaki et al., "Construction of Three-dimensional Vascularized Functional Human Liver Tissue using a Layer-by-Layer Cell Coating Technique" Biomaterials, Feb. 28, 2017, 133:263-274.
Nahmias et al., "Endothelium-Mediated Hepatocyte Recruitment in the Establishment of Liver-like Tissue In Vitro". Tissue Engineering, 2006, vol. 12(6), pp. 1627-1638.
Okudaira et al., "Fabrication of a Fiber-type Hepatic Tissue by Bottom-up Method using Multilayer Spheroids", Journal of Bioscience and Bioengineering, 2017, vol. 123(6), pp. 739-747.
Japanese Notice of Reasons for Refusal for Japanese Application No. 2020-516879, dated Jul. 5, 2022, with translation, 11 pages.
Extended European Search Report for European Application No. 18857586.4, dated May 28, 2021, 7 pages.

PLATED HEPATOCYTES AND PREPARATION AND USES THEREOF

CROSS REFERENCE TO RELATED APPLICATIONS

This application is a U.S. National Phase Application of PCT International Application PCT/US2018/052315, filed on Sep. 22, 2018, which claims the benefit of U.S. Provisional Application No. 62/562,127, filed Sep. 22, 2017, the contents of which are incorporated herein by reference in their entireties for all purposes.

FIELD OF THE INVENTION

The invention relates generally to plated human hepatocytes and preparation and uses thereof.

BACKGROUND OF THE INVENTION

Primary human hepatocytes isolated from donors have been used in 2D in vitro culture systems for studying drug metabolism or drug induced liver injury. In 2D in vitro culture systems, primary human hepatocytes are maintained in a culture medium and attach to a surface (e.g., a plate) to generate a monolayer of the hepatocytes suitable for testing drug metabolism, toxicity or viral infection. For 2D in vitro culture systems, isolated primary human hepatocytes having a plateability of at least ≥85% for a prolonged period of time, for example, at least 1, 2, 3, 4, 5, 6, 7, 14, 21, 28, 35, 42 or 49 days, are desirable while isolated primary hepatocytes having a plateability of less than 60% are generally deemed less desirable and not suited for long-term experiments. A high percentage of cryopreserved primary human hepatocyte batches fall into the latter category of non- or poorly plateable hepatocytes that limits the availability of many batches with desirable donor specifications such as nonalcoholic fatty liver disease (NAFLD) and nonalcoholic steatohepatitis (NASH) for the applications such as testing drug metabolism, toxicity or viral infection. There is a need to improve the plateability, functional stability and culture longevity of primary human hepatocytes.

SUMMARY OF THE INVENTION

The present invention relates to plated human hepatocytes and preparation and uses thereof.

A product comprising plated human hepatocytes on a surface is provided. At least 70% of the plated hepatocytes are in one or more hepatocyte clusters on feeder cells. The feeder cells are endothelial cells and fibroblasts and are attached to the surface. In the product, at least 90% of the plated hepatocytes in the one or more, hepatocyte clusters may be in direct hepatocyte-hepatocyte contact. The one or more hepatocyte clusters may cover at least 50% of the surface. The surface may have a shortest diameter of at least 3 mm.

The product may further comprise a culture medium, and at least 90% of the plated hepatocytes remain on the surface for at least 7 or 42 days.

The plated hepatocytes may produce albumin and/or express cytochrome P450.

The endothelial cells may be human cells. For example, the endothelial cells may be human umbilical vein endothelial cells (HUVEC). The endothelial cells may not be liver cells. The endothelial cells may not proliferate. The endothelial cells may be primary cells or cultured up to 7 passages. The endothelial cells may not be immortal.

The fibroblasts may be human cells. The fibroblasts may be human dermal fibroblasts. The fibroblasts may not be liver cells. The fibroblasts may not proliferate. The fibroblasts may be primary cells or cultured up to 7 passages. The fibroblasts may not be immortal.

In the product, the plated hepatocytes, the endothelial cells and the fibroblasts may have a cell ratio from 3:1:1 to 24:1:1.

The plated hepatocytes may be obtained from a single donor. The plated hepatocytes may be obtained from two or more donors. Each donor may have suffered from microsteatosis and/or nonalcoholic steatohepatitis (NASH).

A method of preparing plated human hepatocytes is also provided. The preparation method comprises applying human hepatocytes to a surface in the presence of feeder cells, which are endothelial cells and fibroblasts, co-culturing the applied hepatocytes with the feeder cells after the applying step, and forming one or more hepatocyte clusters by the co-cultured hepatocytes on the feeder cells, which are attached to the surface. At least 85% of the co-cultured hepatocytes are in the one or more hepatocyte clusters. The applied hepatocytes may have a plateability of less than 60% on the surface in the absence of the feeder cells. The applied hepatocytes may have a plateability of at least 85% on the surface in the absence of the feeder cells. The one or more plated hepatocyte clusters may cover at least 50% of the surface. The surface may have a shortest diameter of at least 3 mm.

According to the preparation method, at least 90% of the plated hepatocytes may remain on the surface for at least 7 or 42 days. The feeder cells may be attached to the surface before the applying step or in the co-culturing step. The hepatocytes may be frozen before the applying step.

The preparation method may exclude addition of an extracellular matrix protein.

For each preparation method, plated hepatocytes prepared according to the method are provided.

A method of testing a pharmaceutical substance is provided. The method comprises administering a pharmaceutical substance to plated hepatocytes in an amount effective to change a property of the plated hepatocytes. The plated hepatocytes may be in the product of the present invention or prepared according to the method of the present invention. The pharmaceutical substance may be selected from the group consisting of small molecules, antibodies, live viruses, viral vectors, oligonucleotides and cells.

A method of testing drug metabolism is provided. The method comprises administering an effective amount of a drug to plated hepatocytes, and determining the amount of the drug in the plated hepatocytes. The plated hepatocytes may be in the product of the present invention or prepared according to the method of the present invention.

A method of testing drug transport is provided. The method comprises administering an effective amount of a drug to plated hepatocytes, and determining the location of the drug in the plated hepatocytes. The plated hepatocytes may be in the product of the present invention or prepared according to the method of the present invention.

A method of testing drug toxicity is provided. The method comprises administering an effective amount of a drug to plated hepatocytes, and detecting viable plated hepatocytes. The plated hepatocytes may be in the product of the present invention or prepared according to the method of the present invention.

A method of preparing a hepatitis B virus (HBV) infected hepatocyte culture model is provided. The method comprises inoculating plated hepatocytes with hepatitis B virus (HBV), and incubating the infected plated hepatocytes for at least 14 days. The plated hepatocytes may be in the product of the present invention or prepared according to the method of the present invention.

A kit for plating hepatocytes is provided. The kit comprises a first cryovial comprising primary hepatocytes, a second cryovial comprising endothelial cells, a third cryovial comprising fibroblasts, and an instruction for preparing plated human hepatocytes with the primary hepatocytes, the endothelial cells and the fibroblasts according to the method of the present invention. The second cryovial and the third cryovial may be the same. The first cryovial, the second cryovial and the third cryovial may be the same.

DETAILED DESCRIPTION OF THE INVENTION

Figure 1:
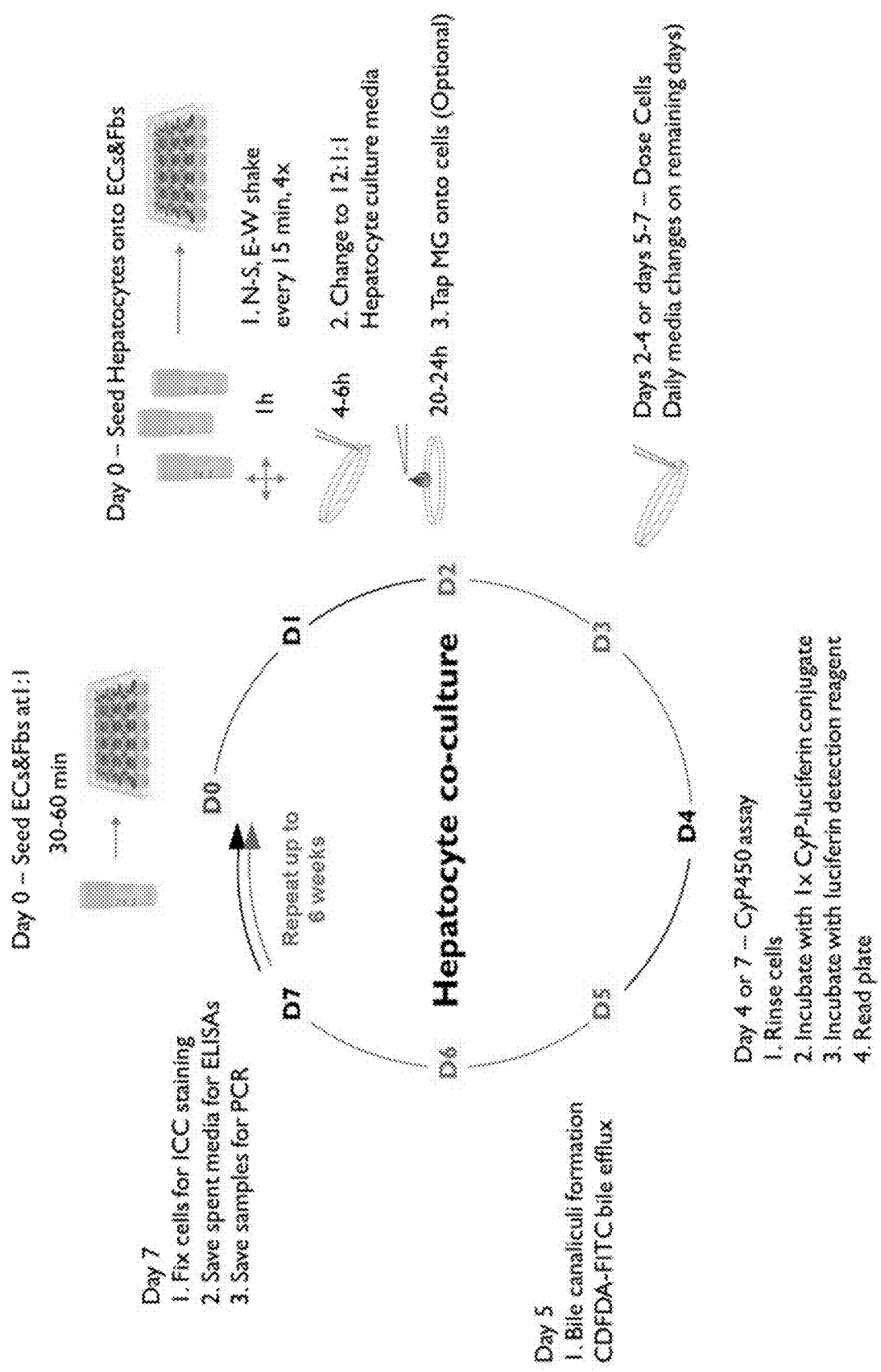
FIG. 1 shows schematic #1 for a human hepatocyte co-culture according to one embodiment of the invention. This schematic provides the preparation of the cell culture and analysis with a timeframe. According to schematic #1, the hepatocyte co-culture is prepared by seeding human hepatocytes onto pre-plated feeder cells, which are endothelial cells and fibroblasts, on day 0. ECs, endothelial cells; Fbs, fibroblasts; MG, MATRIGEL.

The present invention provides plated hepatocytes and preparation and uses thereof. The invention is based on the discovery that co-culturing human hepatocytes with endothelial cells and fibroblasts improves plateability, functional stability and culture longevity of the human hepatocytes.

The term "plated hepatocytes" used herein refers to human hepatocytes attached to a surface or a feeder cell layer, either directly or indirectly. The term terms "plateability" or "plateable" used herein refers to the ability of hepatocytes to attach to a surface such as a plastic or treated surface (e.g., a culture vessel or multiwell plate), for example, within a predetermined period of time (e.g., 0.5, 1, 2, 3, 4, 5, 6 or 12 hours) upon exposure of the hepatocytes to the surface. The plateability of hepatocytes may be characterized by a percentage of the cells capable of being attached to the surface, directly or indirectly via, for example, feeder cells or non-cell substances (i.e., substances that are not cells), within a predetermined period of time.

The term "feeder cells" used herein refers to cells other than hepatocytes that assist the hepatocytes to remain viable and functional. Examples of feeder cells include fibroblasts and endothelial cells. Non-cell substances may be chemical compounds and/or biological molecules. Examples of non-cell substances include extracellular matrix proteins, hemodynamic flow conditions, paracrine and autocrine factors, adhesion proteins, and polysaccharides.

Hepatocytes may be deemed plateable if at least 70%, 75%, 80%, 85%, 90%, 95%, 99% or 100% of the cells are capable of being attached to a surface, for example, within a pre-determined period of time.

Hepatocytes may be deemed non- or poorly plateable if no more than 70%, 65%, 60%, 55%, 50%, 45% or 40% of the cells are capable of being attached to a surface, for example, within a pre-determined period of time.

The term "hepatocyte cluster" used herein refers to a group of two or more hepatocytes in a 3D structure. At least about 70%, 80%, 90%, 95% or 99% of the hepatocytes in the hepatocytes may be in direct hepatocyte-hepatocyte contact, which may be evidenced by the presence of gap junction proteins (e.g., Connexin 32) or tight-gap junction associated proteins (e.g., occludin, ZO-1, claudin-1 and claudin-4).

In addition to cell-cell interactions and the presence of cellular junctions, the overall shape and 3D architecture of the hepatocytes in the co-culture system maintain their normal structure and function, including cell signaling pathways and normal gene expression program. The co-culture system sustains the overall 3D architecture and shape of the hepatocytes over time thus enhancing their cell-cell interactions and preventing cell spreading and the loss of the normal hepatic phenotype. In contrast, hepatocytes maintained as mono-cultures, especially at subconfluent conditions, lose their cell shape and architecture over time and begin to spread and become 'thinner' (lose their height) in the absence of the surrounding stromal cells and their supporting ECM factors. This deterioration in cell shape with extensive cell spreading the hepatocytes begin to show a corresponding reduction and loss of key functions, change in gene expression program, and altered response to drug compounds.

The term "functional stability" or "functional stable" used herein refers to the stability of one or more basic hepatocyte functions of hepatocytes over a predetermined period of time. The basic hepatocyte functions include albumin and urea synthesis rates, cytochrome P450 enzyme activity rates, and inducible cytochrome P450 levels. The functional stability of hepatocytes may be characterized by a percentage of a basic function of the cells initially, for example, within an initial period of time after isolation from a donor, for example, during the initial 4 to 6 days, being maintained in culture after the predetermined period of time, for example, subsequent 1, 2, 3, 4, 5 or 5 days or 1, 2, 3, 4, 5, 6, 7, 8, 9 or 10 weeks (e.g., up to 28 or 42 days). Hepatocytes are deemed functionally stable if at least 50%, 60%, 70%, 80%, 90%, 95% or 99% of a basic hepatocyte function of the cells is retained after the predetermined period of time, for example, without more than 5, 10, 15, 20 or 25% deviation.

The term "culture longevity" used herein refers to the lifetime of hepatocytes that remain viable and functional. Cells attached to the surface are also referred to as plated cells. At least 70%, 75%, 80%, 85%, 90%, 95%, 99% or 100% of the plated cells may remain viable while attached to the surface for a predetermined period of time, for example, 1, 2, 3, 4, 5 or 6 days or 1, 2, 3, 4, 5, 6, 7, 8, 9 or 10 weeks. Viable hepatocytes are functional as evidenced by, for example, production of albumin and urea, and cytochrome P450 enzymatic activity.

The term "hepatocytes" as used herein refers to primary liver cells that have been isolated or obtained from one or more donors and that have not been cultured for a predetermined number of passages (e.g., 0, 1, 2, 3, 4 or 5 passages). The term "pooled hepatocytes" as used herein refers to primary hepatocytes isolated from two or more donors and then mixed. The hepatocytes can be selected from donors based on certain genotyping information.

The term "donor" used herein refers to a living mammal having a liver. The mammal may be a human, a cow, a pig, a dog, a cat, a non-human primate, a rodent such as a rat or mouse, a horse, a goat, a sheep, or a deer. The donor may be a human who has suffered from a liver disease or condition, for example, microsteatosis, nonalcoholic steatohepatitis (NASH), Non-alcoholic fatty liver disease (NAFLD) or hepatitis (e.g., A, B, C, D and E). Hepatocytes from NASH disease liver may express markers such as cyto-keratin 18.

The term "endothelial cells" used herein refers to any endothelial cells. The endothelial cells may be primary human cells, for example, human umbilical vein endothelial cells (HUVEC). The endothelial cells may not be liver cells. The endothelial cells can be isolated from umbilical cord, liver, lung, kidney, brain, spleen, lymph node, heart, intestine or other arteries, veins or capillary vessels. The endothelial cells may not proliferate. The endothelial cells may be primary cells or cultured up to 1, 2, 3, 4, 5, 6, 7, 8, 9, 10, 11, or 12 passages. The endothelial cells may not be immortal.

The term "fibroblasts" used herein refers to any fibroblasts. The fibroblasts may be primary human cells, for example, human dermal fibroblasts. The fibroblast may be isolated from skin, lung, bladder, cornea, or other tissue types. The fibroblasts may not be liver cells. The fibroblasts may not proliferate. The fibroblasts may be primary cells or cultured up to 1, 2, 3, 4, 5, 6, 7, 8, 9, 10, 11, or 12 passages. The fibroblasts may not be immortal.

Feeder cells may be prepared by the inactivation and freezing of cultured dermal fibroblasts and HUVECs at or before seven passage in culture. Inactivation of the feeder cells may be completed with mitomycin C or gamma irradiation and then verified through either PCNA or BrdU or cell counting. Inactive feeder cells may be frozen for the preparation of one plate of co-culture per vial. Each lot of feeder cells may be tested to ensure the quality criteria such as but not limited to cell number, viability, cell doubling time, sterility, and purity. The fibroblasts and endothelial cells used herein may have no or low interferences with the hepatocytes used herein. The term "interference" used herein refers to typical characteristics, for example, biological activities, of hepatocytes. For example, the fibroblasts and endothelial cells may have no more than about 0%, 0.1%, 0.5%, 1%, 2%, 3%, 4%, 5%, 7%, 10%, 20%, 30% or 40% of the albumin secretion, metabolic clearance, induction, transporter activities or other biological activities of the hepatocytes used in the co-culture. The fibroblasts and endothelial cells may have a cell viability of about 70%, 75%, 80%, 85%, 90%, 95%, 99%, or higher. The ratio of fibroblasts to endothelial cells such as HUVECs may be in the range from about 1:10 to about 10:1, for example, about 1:1, 1:2, 2:1 or any other desirable ratio, as evidenced by, for example, the expression of a fibroblast marker (e.g., TE-7) and an endothelial marker (e.g., CD31). The feeder cells may be free of mycoplasma and endotoxin.

The term "co-culture" as used herein refers to a culture comprising two or more types of cells in a culture medium. The term "hepatocyte co-culture" as used herein refers a culture comprising hepatocytes and feeder cells, which are endothelial cells and fibroblasts, in a culture medium. A cell ratio of the hepatocytes and the feeder cells may be in the range from about 1:40 to about 40:1 while a cell ratio of the fibroblast cells and the endothelial cells in the feeder cells may be in the range from about 1:10 to about 10:1. A cell ratio of the hepatocytes, the endothelial cells and the fibroblasts may be from 3:1:1, 6:1:1, 12:1:1 to 24:1:1. The cell ratio of the hepatocytes and the feeder cells and the cell ratio of the fibroblasts and the endothelial cells in the feeder cells may be adjusted to improve plateability or longevity of the hepatocytes in the co-culture.

A composition comprising cells in a culture medium is provided. The cells may consist of hepatocytes (e.g., human hepatocytes) and feeder cells, which may include endothelial cells and fibroblasts. The hepatocytes may be plateable. The hepatocytes may be functionally stable. The hepatocytes may have culture longevity.

Cells are commonly cultured in a culture medium developed to promote a desirable property (e.g., growth) of the cells. Hepatocytes are typically cultured in hepatocyte plating media within a desirable cell concentration range. Fibroblasts are typically cultured in fibroblast media within a desirable cell concentration range. Endothelial cells are typically cultured in endothelial cell media within a desirable cell concentration range. When the hepatocytes are co-cultured with the endothelial cells and the fibroblasts, the hepatocyte plating media, the fibroblast media and the endothelial cell media will contribute to a co-culture plating media used for plating and/or co-culturing the cells.

To achieve a desirable cell ratio of the hepatocytes to the endothelial cells and the fibroblasts, the composition of the co-culture plating media can be adjusted. The co-culture plating media may comprise the hepatocyte plating media, the fibroblast media and the endothelial cell media at a volume ratio of about (5-30):(1-5):(1-5), for example, from about 10:1:1 to about 20:1:1. In one embodiment, the co-culturing plating media may have a ratio of the hepatocyte media, the endothelial cell media and the fibroblast at 12:1:1, which means twelve parts of the hepatocyte plating media, one part of the endothelial cell media, and one part of the fibroblast media.

The hepatocyte plating media may be DMEM (Dulbecco's Modified Eagle Medium, Gibco 21063-029) supplemented with 10% heat-inactivated FBS (Gibco 10082-147), 1× NEAA (Non-essential amino acids, Sigma M7145), 1 mM sodium pyruvate (Gibco 11360-070), 5 µg/mL of Insulin, and 5 µM Dexamethasone. The hepatocyte plating media may be WEM (William's E Media, Gibco A1217601) supplemented with 10 mM HEPES (Fisher BP299100), 1× Glutamax (Gibco 35050061), 1× ITS-A (Gibco 51300-044), and 10 µM Dexamethasone The endothelial cell media may be purchased from Life-Line. The endothelial cell media may be VasulLife Basal Medium, 5 ng/mL, rh-FGF-b, 50 µg/mL Ascorbic Acid, 1 µg/mL Hydrocortisone, 2% FBS, 10 mM L-Glutamine, 15 ng/mL rh IGF-1, 5 ng/mL rh EGF, 5 ng/mL rh VEGF, and 0.75 U/mL Heparin Sulfate.

The fibroblast media may be DMEM high glucose (Gibco 11995-065) supplemented with 10% FBS.

In one embodiment, at least 70%, 75%, 80%, 85%, 90%, 95%, 99% or 100, for example, at least 85%, of the hepatocytes are plateable in the presence of the endothelial cells and the fibroblast cells. In another embodiment, less than 100%, 90%, 80%, 70%, 60%, 50%, 40%, 30%, 20% or 10%, for example, less than 60%, of the hepatocytes may be plateable in the absence of the endothelial cells and the fibroblasts.

The hepatocytes (e.g., human hepatocytes) in the composition may be plated. At least 70%, 75%, 80%, 85%, 90%, 95%, 99% or 100%, for example, 90%, of the plated hepatocytes may remain viable and functional while attached to the surface for a predetermined period of time, for example, at least 1, 2, 3, 4, 5, 6, 7, 14, 21, 28, 35, 42 or 49 days, for example, at least 7 or 42 days.

A product comprising plated human hepatocytes on a surface is provided. At least 40%, 50%, 60%, 70%, 75%, 80%, 85%, 90%, 95%, 99% or 100, for example, at least 70%, of the plated hepatocytes are in one or more hepatocyte clusters on feeder cells. The feeder cells are endothelial cells and fibroblasts and are attached to the surface. At least 70%, 75%, 80%, 85%, 90%, 95%, 99% or 100, for example, at least 90%, of the plated hepatocytes in the one or more hepatocyte clusters may be in direct hepatocyte-hepatocyte contact. The one or more hepatocyte clusters may cover at least 40%, 50%, 60%, 70%, 75%, 80%, 85%, 90%, 95%, 99% or 100, for example, at least 50%, of the surface. The surface may have a shortest diameter of at least 0.5, 1, 2, 3, 4, 5, 6, 7, 8, 9, 10 or 100 mm.

The product may further comprise a culture medium. The culture medium may a mixture of a hepatocyte plating medium, an endothelial cell medium and a fibroblast medium. At least 70%, 75%, 80%, 85%, 90%, 95%, 99% or 100, for example, at least 90%, of the plated hepatocytes remain on the surface for at least 3, 4, 5, 6, 7, 14, 21, 28 or 42 days.

The plated hepatocytes may exhibit one or more basic hepatocyte functions of hepatocytes. For example, the plated hepatocytes may produce albumin and/or express cytochrome P450.

The endothelial cells may be human cells. For example, the endothelial cells are human umbilical vein endothelial cells (HUVEC). The endothelial cells may not be liver cells. The endothelial cells may not proliferate. The endothelial cells may be primary cells or cultured up to 3, 4, 5, 6, 7, 8, 9 or 10, for example, 7 passages. The endothelial cells may not be immortal.

The fibroblasts may be human cells. The fibroblasts may be human dermal fibroblasts. The fibroblasts may not be liver cells. The fibroblasts may not proliferate. The fibroblasts may be primary cells or cultured up to 3, 4, 5, 6, 7, 8, 9 or 10, for example, 7, passages. The fibroblasts may not be immortal.

In the product, the plated hepatocytes, the endothelial cells and the fibroblasts may have any cell ratio that improves the plateability of the hepatocytes, for example, from 3:1:1, 6:1:1, 12:1:1 to 24:1:1

The plated hepatocytes may be obtained from a single, two or more donors. Each donor may have suffered from a liver disease or disorder, for example, microsteatosis or nonalcoholic steatohepatitis (NASH).

A method of preparing plated human hepatocytes is provided. The preparation method comprises applying human hepatocytes to a surface in the presence of feeder cells, which are endothelial cells and fibroblasts, co-culturing the applied hepatocytes with the feeder cells after the applying step, and forming one or more hepatocyte clusters by the co-cultured hepatocytes on the feeder cells, which are attached to the surface. At least 40%, 50%, 60%, 70%, 75%, 80%, 85%, 90%, 95%, 99% or 100, for example, at least 70%, of the co-cultured hepatocytes are in the one or more hepatocyte clusters.

The applied hepatocytes may have a platability of less than 70%, 65%, 60%, 55%, 50%, 45% or 40%, for example, less than 60%, on the surface in the absence of the feeder cells. The applied hepatocytes may have a platability of at least 70%, 75%, 80%, 85%, 90%, 95%, 99% or 100%, for example, at least 85%, on the surface in the absence of the feeder cells.

The one or more hepatocyte clusters may cover at least 40%, 50%, 60%, 70%, 75%, 80%, 85%, 90%, 95%, 99% or 100, for example, at least 50%, of the surface. The surface may have a shortest diameter of at least 0.5, 1, 2, 3, 4, 5, 6, 7, 8, 9, 10 or 100 mm. At least 70%, 75%, 80%, 85%, 90%, 95%, 99% or 100, for example, at least 90%, of the plated hepatocytes in the one or more hepatocyte clusters may be in direct hepatocyte-hepatocyte contact.

At least 70%, 75%, 80%, 85%, 90%, 95%, 99% or 100%, for example, at least 90%, of the plated hepatocytes remain plated, i.e., attached to the surface, in the presence of the endothelial cells and the fibroblasts for a predetermined period of time, for example, for at least 1, 2, 3, 4, 5, 6, 7, 14, 21, 28, 35, 42 or 49 days, for example, 7 or 42 days. The hepatocytes may be co-cultured with the endothelial cells and the fibroblasts for no more than 10, 9, 8, 7, 6, 5, 4, 3, 2 or 1 day(s), for example, no more than 3 days.

According to the preparation method of the present invention, the endothelial cells and/or the fibroblasts may be attached to the surface before, when or after the hepatocytes are attached to the surface. The endothelial cells and/or the fibroblasts may be attached to the surface before or during the co-culturing step.

The preparation method may exclude additional extracellular matrix proteins. The additional extracellular matrix proteins may be selected from the group consisting of collagen matrix, e.g. BioCoat, or rat tail collagen, HuGentra Matrix, MATRIGEL and HuBiogel.

The preparation method may further comprise freezing the plated hepatocytes.

For each preparation method, the prepared plated hepatocytes are provided.

A method of testing a pharmaceutical substance is provided. The method comprises administering a pharmaceutical substance to plated hepatocytes in an amount effective to change a property of the plated hepatocytes. The plated hepatocytes may be in the product of the present invention or prepared according to the method of the present invention. The pharmaceutical substance may be selected from the group consisting of small molecules, antibodies, live viruses (e.g., hepatitis B or C), viral vectors, oligonucleotides and cells.

A method of testing drug metabolism is provided. The method comprises administering an effective amount of a drug to plated hepatocytes. The plated hepatocytes may be in the product of the present invention or prepared according to the method of the present invention. The term "drug metabolism" as used herein refers to conversion or clearance of a drug. The method further comprises determining the amount of the drug in the plated hepatocytes.

A method of testing drug transport is provided. The method comprises administering an effective amount of a drug to plated hepatocytes. The plated hepatocytes may be in the product of the present invention or prepared according to the method of the present invention. The method further comprises determining the cellular uptake and distribution of the drug in the plated hepatocytes.

A method of testing drug toxicity is provided. The method comprises administering an effective amount of a drug to plated hepatocytes. The plated hepatocytes may be in the product of the present invention or prepared according to the method of the present invention. The method further comprises detecting a toxic event. The detection of a toxic event may be evidenced by a reduced percentage of remaining viable plated hepatocytes.

A method of preparing a hepatitis B virus (HBV) infected hepatocyte culture model is provided. The method comprises inoculating plated hepatocytes with hepatitis B virus (HBV), and incubating the infected plated hepatocytes for at least 7, 14 or 21 days, for example, 14 days. The HBV infected hepatocyte culture model is prepared. The plated hepatocytes may be in the product of the present invention or prepared according to the method of the present invention. The method may further compromise determining transcription or expression level of a liver-specific bile acid transporter, for example, sodium taurocholate cotransporting polypeptide (NTCP), of hepatocytes, selecting a batch of hepatocytes with a desirable transcription or expression level of NTCP, plating the selected batch of hepatocytes according to the method of current invention before inoculating the plated hepatocytes with hepatitis B virus (HBV). An overlay of protein matrix may not be needed with the current invention to increase the virus inoculation efficiency. A suspension grade hepatocyte batch with a desirable NTCP level may be used for HBV inoculation and suitable for long-term culture studies.

A kit for plating hepatocytes according the present invention is provided. The kit comprises a first cryovial comprising primary hepatocytes, a second cryovial comprising endothelial cells, a third cryovial comprising fibroblasts, and an instruction for preparing plated human hepatocytes with the primary hepatocytes, the endothelial cells and the fibroblasts according to the method of the present invention. The second cryovial and the third cryovial may be the same. The first cryovial, second cryovial and the third cryovial may be the same. The kit may comprises hepatocyte cryovial from a single donor, or hepatocyte cryovials from multiple donors. The kit comprises test results or certificate of analysis (COA) for the hepatocyte co-culture system. The kit comprises a user instruction protocol for preparation methods. The kit comprises culture mediums for thawing, plating, and culturing the hepatocytes, fibroblasts and endothelial cells.

A method for preparing a hepatocyte co-culture system is provided. The method comprises isolating hepatocytes from a liver of a donor, adding fibroblasts and endothelial cells to the isolated hepatocytes, and freezing hepatocytes mixed with fibroblasts and endothelial cells. The method may further comprise growing cells in culture, wherein the cells consist of the hepatocytes, the fibroblasts and the endothelial cells. The donor may be an animal, preferably a human.

Figure 27:
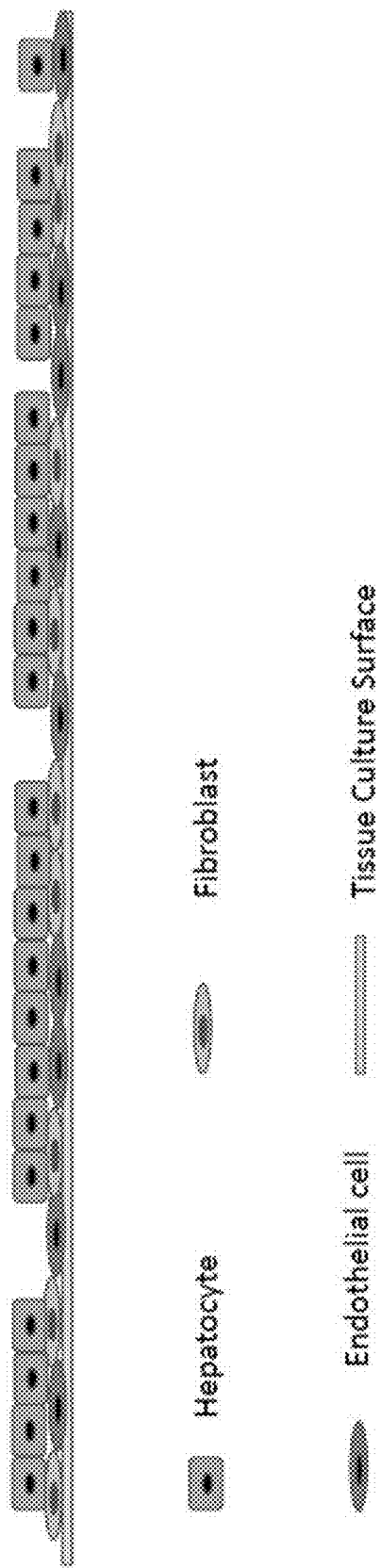
FIG. 27 is schematic diagram of a co-culture system according to one embodiment of the invention.

A ready-to-use hepatocyte co-culture system is provided. The co-culture hepatocyte system comprises a tissue culture plate with a culture well or culture wells with or without ECM substrate coating, a fibroblast and endothelial cell layer attached to the surface of the culture well, and a hepatocyte layer attached on the fibroblasts and endothelial cells or cell layer, forming hepatocyte clusters or hepatocyte islands. The hepatocyte clusters, also known as hepatocyte islands, are self-assembled after seeding onto or with the fibroblasts and endothelial cells. The hepatocytes within the hepatocyte clusters or hepatocyte islands maintain direct hepatocyte-hepatocyte contact. And the hepatocytes produce hepatocyte-hepatocyte adhesion molecules such as cadherins and connexins. Higher than 70%, 75%, 80%, 85%, 90%, 95% or 99% of the hepatocytes in the co-culture system will distribute in the hepatocyte clusters and maintain direct hepatocyte-hepatocyte contact. Higher than 20%, 25%, 30%, 40%, 50%, 60%, 70%, 75%, 80%, 85%, 90%, 95% or 99% of the surface of the culture well is covered by the hepatocyte clusters. The hepatocytes used herein can be from a single donor, or from multiple donors. And the endothelial cells in the co-culture system may form vessel like structure during culture (FIG. 27).

Example 1

Co-Cultured Human Hepatocytes

Human primary hepatocytes co-cultured with human dermal fibroblasts and endothelial cells were characterized. In this example, suspension grade hepatocytes had a plateability of less than 70% while plateable grade hepatocytes had a plateability of at least 70%.

1. Methods 1.1 Isolation and Cryopreservation of Human Primary Hepatocytes

Human primary hepatocytes were isolated from human donors and then stored in liquid nitrogen.

1.2 Source of Human Dermal Fibroblasts and Endothelial Cells

Human dermal fibroblasts were isolated from adult skin and characterized by TE-7 expression. Human umbilical vein endothelial cells (HUVECs) were isolated from umbilical cord and characterized by CD31 and vascular endothelial (VE)-cadherin expressions. Immortalized human liver sinusoidal endothelial cells (SECs) were purchased from abm Inc. Bathe dermal fibroblasts and endothelial cells were frozen at passage #0 or #1 in freezing medium containing 10% DMSO (Sigma).

1.3 Preparation of Inactive Feeder Cell Layer for Co-Culture

Adult dermal fibroblasts were propagated and grown to confluency in DMEM (Dulbecco's Modified Eagle Medium, Gibco) high glucose supplemented with 10% fetal bovine serum. Both HUVECs and SECs were grown to confluency in endothelial cell proliferation medium purchased from Lonza. Once confluent, cells were passaged by an enzymatic digestion with TryPLE (Gibco) or Trypsin-EDTA (Gibco). Either enzyme was used to detach the cells from the tissue culture surface and create a suspension of the cells, which could be counted. The cells in suspension were then seeded at a lower density by increasing the volume of the cell suspension and transferring the cell suspension to a greater surface area of tissue culture plastic than they were previously seeded. Cells were seeded at a density from 10,000 to 15,000 cells/cm$^2$ and passaged once the cells reached confluency, about every five to seven days. Cells were passaged for a maximum of five times before they were mitotically inactivated and frozen.

Because Mitomycin C or Gamma irradiation inactivates cells by causing double strand breaks, Mitomycin C was used to inactive confluent fibroblasts and/or endothelial cells. The inactive cells were mitotically inactive and did not proliferate. Briefly, the cells were rinsed three times with Dulbecco's phosphate-buffered saline (DPBS, Gibco, Paisley, UK), incubated with 10 µg/ml of Mitomycin C (Sigma) for 3 hours at 37° C., and then rinsed three times with DPBS. After inactivation, the fibroblasts and endothelial cells were immediately dissociated with TryPLE for cell counts and then resuspended in a cryopreservation medium at a concentration of 1-2 million cells/ml. The cells were then aliquoted into cryovials, and stored at −80° C. overnight. On the following day, the cells were transferred to liquid nitrogen conditions for long-term storage.

1.4 Plating of Suspension Grade and Plateable Grade Human Hepatocytes onto Inactive Feeder Cells, Mixture of Endothelial Cells and Fibroblasts Feeder cells consisting of human dermal fibroblasts and endothelial cells were thawed and seeded at 25,000 cells/cm$^2$ either onto a collagen-coated (BioCoat, Corning) or no matrix-coated general tissue culture plastic 24- or 96-well plates. The tested feeder cell densities were from 12,500 cells/cm$^2$ to 100,000 cells/cm$^2$).

30 minutes after seeding the feeder cells, primary human hepatocytes were seeded at 150,000 cells/cm$^2$ (Schematic #1). Traditionally, hepatocytes are seeded at 250,000 cells/cm$^2$ onto a collagen coated tissue culture plate. The hepatocyte cellular density may be adjusted in the co-culture system to allow for more or less hepatocyte interaction as well as to account for the attachment rate of the hepatocytes.

Alternatively, the feeder cells and hepatocytes can be plated together by mixing the hepatocytes and feeder cells into a homogenous suspension, and then seeding the feeder cells and hepatocytes together onto a collagen-coated plate (Schematic #2). 4-6 hours after seeding the hepatocytes, the medium was changed to remove unattached cells and cellular debris. The incubation time or shaking condition before medium change can vary depend on the type of culture plate (for example, 6-well, 12-well, 24-well 48-well, 96-well, or 384-well plates) used.

16-20 hours after seeding the hepatocytes, an extra cellular matrix, such as MATRIGEL, was tapped onto the culture for hepatocyte maturation induction. The culture platform was successful without the addition of an extra cellular matrix.

1.5 Long-Term Culture of Hepatocytes under Co-Culture Condition

The traditional plateable hepatocyte monoculture model allows for up to 7 days of culture and analysis of high grade hepatocytes, which begin to spread out due to breakdown of their membranes and end up losing their functionality. The plateable grade hepatocytes and the suspension grade hepatocytes were seeded onto feeder cells in the co-culture model to study their morphology and function up to 6 weeks. The medium was changed daily throughout the culture period. The hepatocyte culture medium contained HEPES (Fisher), GlutaMAX (Gibco), ITS+ (Insulin, transferrin, selenium complex, BSA and linoleic acid, Gibco), dexamethasone (Sigma), and odium pyruvate (Gibco) in William's E medium (Gibco).

Throughout the 6 weeks of culture, hepatocytes in co-culture were fed daily with culture medium 12:1:1 HHCM, which is a mixture of hepatocyte culture medium, endothelial cell culture medium, and fibroblast culture medium at a volume ratio of 12:1:1, in studies of their typical cuboidal morphology, bile canaliculi formation, CyP450 enzyme activity, and albumin and urea secretion.

1.5 Pooling Hepatocytes from Multiple Donors Eliminates Donor-to-Donor Variations Hepatocytes vary in their attachment rate, morphology, protein expression, and enzyme functionality largely due to their donors. Hepatocytes from multiple donors, whether of suspension grade or plateable grade, were pooled to determine if pool could reduce or eliminate some of these variations. Hepatocytes from 3-10 or more different donors were thawed individually, counted, and mixed together in equal amounts. The pooled hepatocytes as well as hepatocytes from each donor were seeded separately onto a feeder layer of fibroblasts and endothelial cells at 150,000 cells/cm$^2$. The hepatocytes were pooled together before or after the hepatocytes were frozen.

1.7 Characterization of Hepatocytes in Co-Culture Condition

Hepatocytes of suspension or plateable grade were seeded on inactive feeder cells at 25,000 cells/cm$^2$ and co-cultured for 6 weeks. Their typical cuboidal and multinucleated hepatocyte morphology was visualized by 5-(and-6)-carboxy-2', 7'-dichloro-fluorescein diacetate (CDFDA, Invitrogen) efflux in the bile canaliculi throughout the six weeks of culture.

1.8 CyP450 Activities of Co-Cultured Hepatocytes

The CyP450 1A2, CyP450 2B6, and CyP450 3A4 activities of the co-cultured hepatocytes were analyzed in Promega's P450-Glo™ assays by following the manufacturer's instructions. Samples were induced for 48 hours by 100 μM Omeprezole for CyP450 1A2, 100 nM CITCO for CyP450 2B6, and 25 μM Rifampicin for CyP450 3A4.

When tested over multiple weeks, the samples were allowed to recover for five days, and then the medium was switched back to the induction medium for another 48 hours before analysis. The activity levels in the induced and uninduced samples were analyzed over six weeks.

1.9 Protein and Gene Expression

Spent media samples were collected and evaluated for albumin and urea levels from the co-cultured hepatocytes throughout six weeks of culture. Gene expression levels for albumin, urea, CyP450 1A2, CyP450 2B6, and CyP450 3A4 were assessed weekly throughout the six weeks of culture. The co-culture hepatocytes were fixed after 1 week, 2 weeks, and 6 weeks of culture and stained for albumin, CD31, CD90, CyP450 1A2, CyP450 2B6, and CyP450 3A4.

1.10 Bile Canaliculi Formation

The efflux of 5 (and 6)-carboxy-2',7'-dichlorofluorescein diacetate (CDFDA) was visualized under fluorescence microscope within co-cultured hepatocytes. The co-cultured hepatocytes were rinsed twice with DPBS (—Ca/—Mg), and then incubated with 3:1:1 HHCM at 37° C., 5% $CO_2$ for 10 minutes before being incubated with the 3:1:1 HHCM containing 5 μM CDFDA at 37° C., 5% $CO_2$ for 20 minutes. The cells were then rinsed with DBS (—Ca/—Mg) twice before being imaged in the complete media without phenol red.

2. Schematics for Human Hepatocyte Co-Culture on the Mixture of Endothelial Cells and Fibroblasts: Cell Culture and Analysis with Timeframe 2.1 Schematic #1

In schematic #1, human primary hepatocytes were seeded onto a surface pre-plated with a mixture of endothelial cells and fibroblasts as feeder cells (FIG. 1).

30-60 minutes after seeding the feeder cells, the hepatocytes were added to the feeder cells to establish a hepatocyte co-culture having the hepatocytes, the endothelial cells, and the fibroblast cells at a cell ratio of 3:1:1 in a plating medium mixture of the hepatocyte plating medium, the endothelial cell medium, and the fibroblast cell medium at a volume ratio of 3:1:1, also referred to as 3:1:1 HHPM. The co-cultured cells were placed at 37° C., 5% $CO_2$ and shaken in an N-S and E-W fashion for four times every 15 minutes in the first hour of the hepatocyte co-culture.

4-6 hours after seeding the hepatocytes, the plating medium mixture was changed to a culture medium mixture, of the endothelial cell medium, the fibroblast cell medium and a hepatocyte culture medium at a volume ratio of 3:1:1.

20-24 hours after seeding the hepatocytes, the culture medium mixture became a spent medium and was replaced with fresh mixture of the hepatocyte plating medium, the endothelial cell medium, and the fibroblast cell medium at a volume ratio of 3:1:1, also referred to as 3:1:1 HHCM. If an extracellular matrix such as MATRIGEL, was diluted in the culture medium mixture and added to the cells, the culture medium mixture was subsequently replaced daily with fresh 3:1:1 HHCM.

Cytochrome P450 (CyP450) levels were determined in Promega's P450 Glo™ assays on either day four or day seven.

Bile canaliculi were visualized on day 5 of a one-week assay via the efflux of CDFDA. This assay could be repeated multiple times throughout an extended culture.

Protein expression was detected through immunocytochemical (ICC) staining and ELISAs. ELISAs were used to detect and quantify albumin and urea. The ELISAs were run on 300 μl of the spent media collected after 24 hours of culture. Uninduced and induced samples were fixed for ICC on day 7 and at various time points throughout long-term culture. Cell samples were also snap frozen in Trizol for later RNA extraction and qPCR analysis.

2.2 Schematic #2

Figure 2:
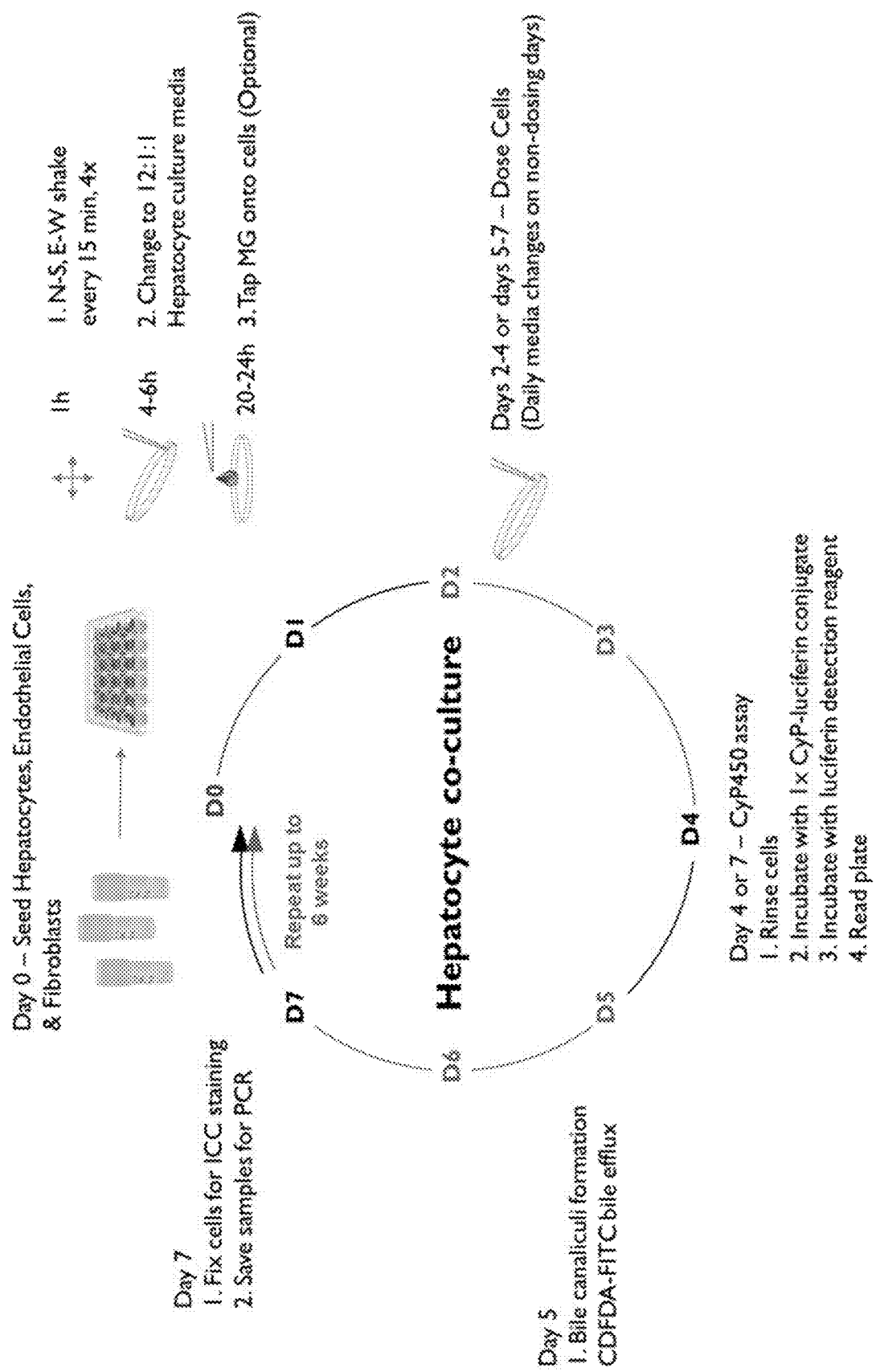
FIG. 2 shows schematic #2 for a human hepatocyte co-culture according to another embodiment of the invention. This schematic provides the preparation of the cell culture and analysis with a timeframe. According to schematic #2, the hepatocyte co-culture is prepared by seeding human hepatocytes together with feeder cells, which are endothelial cells and fibroblasts, on day 0. ECs, endothelial cells; Fbs, fibroblasts; MG, MATRIGEL.

In schematic #2, human primary hepatocytes, endothelial cells, and fibroblasts were seeded together (FIG. 2). Schematic #2 is identical to Schematic #1 except that the non-proliferating feeder cells were mixed with human hepatocytes prior to freezing and then revived at the same time, centrifuged, resuspended, and seeded onto a collagen coated tissue culture plastic plate at a density from 100,000 cells/$cm^2$ to 775,000 cells/$cm^2$ depending on the intended application and the grade of the hepatocytes.

3. Co-Cultured Hepatocytes vs Mono-Cultured Hepatocytes

Human primary hepatocytes were seeded onto feeder cells, a mixture of endothelial cells and fibroblasts, to establish a co-culture under Schematic #1 or 2, or onto a surface in the absence of the feeder cells to establish a mono-culture. There was no significant difference in the hepatocyte properties (e.g., morphology or gene expression) of the co-cultured hepatocytes prepared under Schematic #1 or #2. The co-cultured hepatocytes under Schematic #1 or #2 showed better hepatocyte properties (e.g., morphology or gene expression) than mono-cultured hepatocytes.

Figure 3:
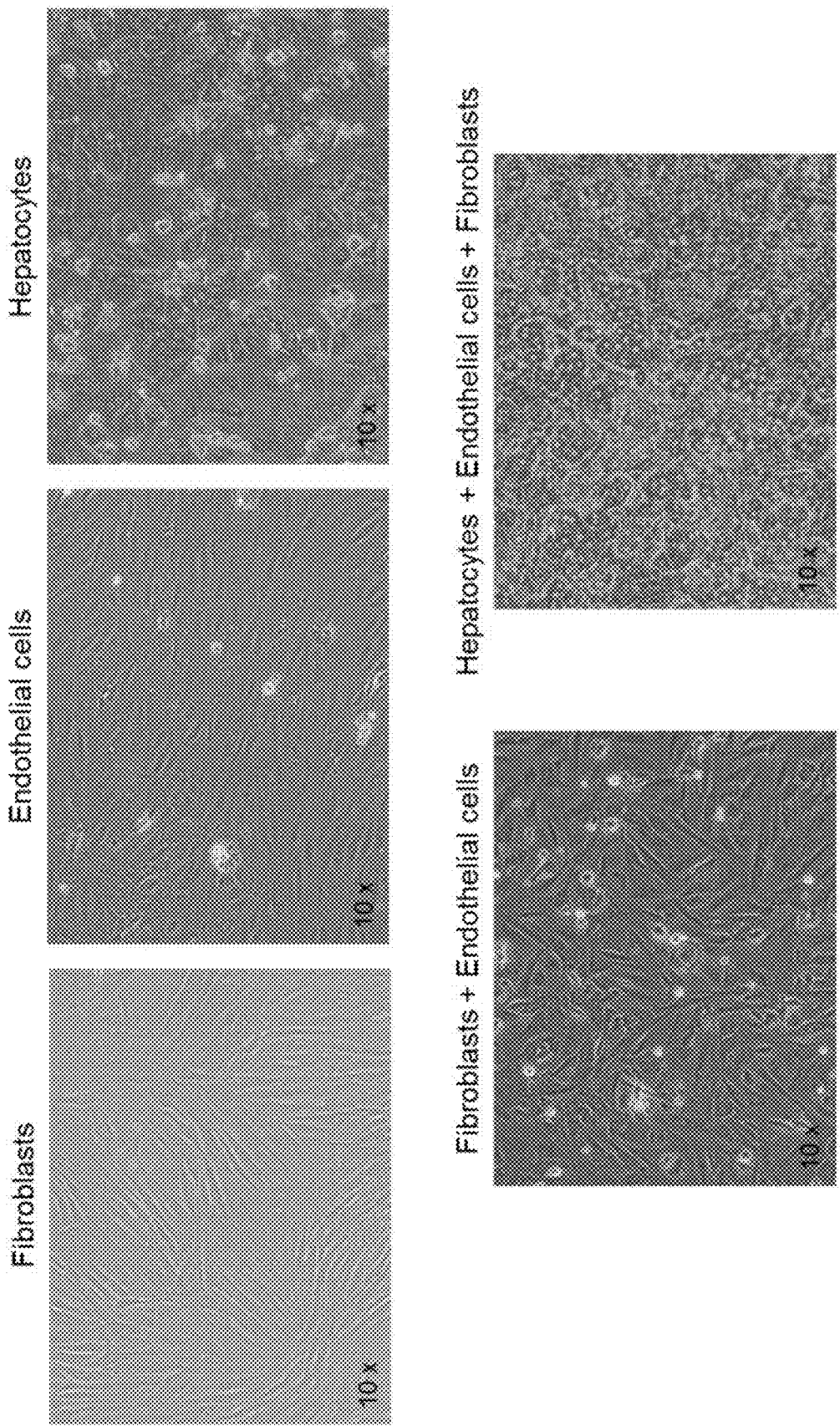
FIG. 3 shows morphology of human cells used for a hepatocyte co-culture: dermal fibroblasts alone (top left), immortalized liver sinusoidal endothelial cells alone (top center), primary hepatocytes alone (top right), a mixture of fibroblasts and endothelial cells (bottom left), and a mixture of primary hepatocytes, endothelial cells and fibroblasts (bottom right).

The co-cultured hepatocytes showed better culture longevity and more hepatocyte morphology compared to mono-cultured hepatocytes (FIG. 3).

Figure 4:
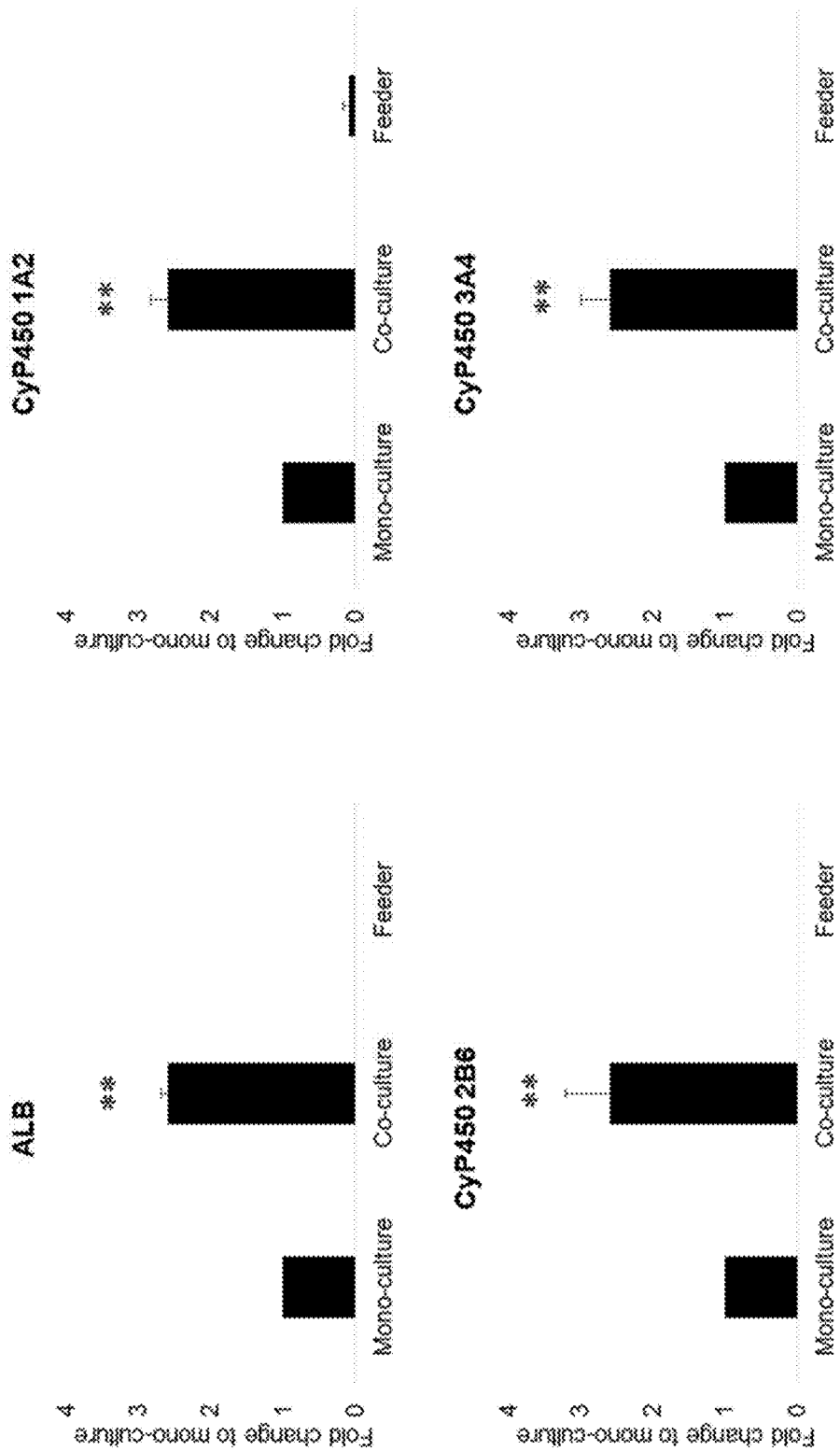
FIG. 4 shows expression levels of albumin, CyP450 1A2, CyP450 2B6, and CyP450 3A4 genes in a hepatocyte mono-culture (mono-culture), a hepatocyte co-culture with feeder cells (co-culture), or a feeder cell culture (feeder) a week after plating as measured by qRT-PCR. The expression level of each of these four genes was significantly higher in the co-culture than the mono-culture. *, $p<0.05$; **, $p<0.01$.

The co-cultured hepatocytes showed significantly higher gene expression of CyP450 1A2, CyP450 2B6, and CyP450 3A4 on day 7 compared to mono-cultured hepatocytes (FIG. 4).

Figure 5:
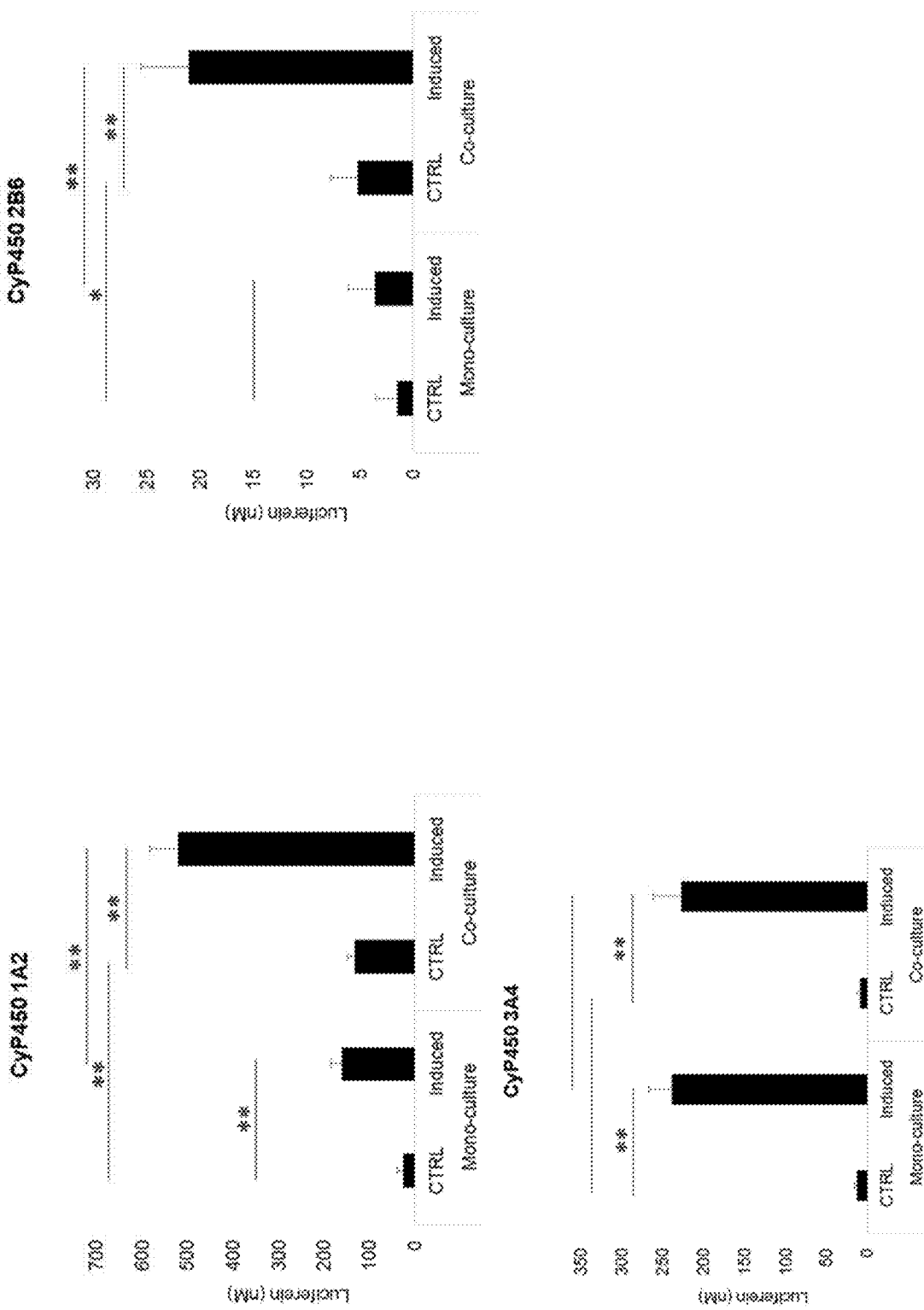
FIG. 5 shows normalized CyP450 1A2, CyP450 2B6, or CyP450 3A4 activities based on seeded hepatocyte numbers in mono-culture or co-culture seven days after plating before and after induction. *, $p<0.05$; **, $p<0.01$.

The co-cultured hepatocytes showed much higher CyP450 1A2 activity and CyP450 2B6 activity after induction for 48 hours mono-cultured hepatocytes on day 7. Additionally, on day 7, the co-cultured hepatocytes showed induced CyP450 3A4 activity similar to the mono-cultured hepatocytes (FIG. 5).

Figure 6:
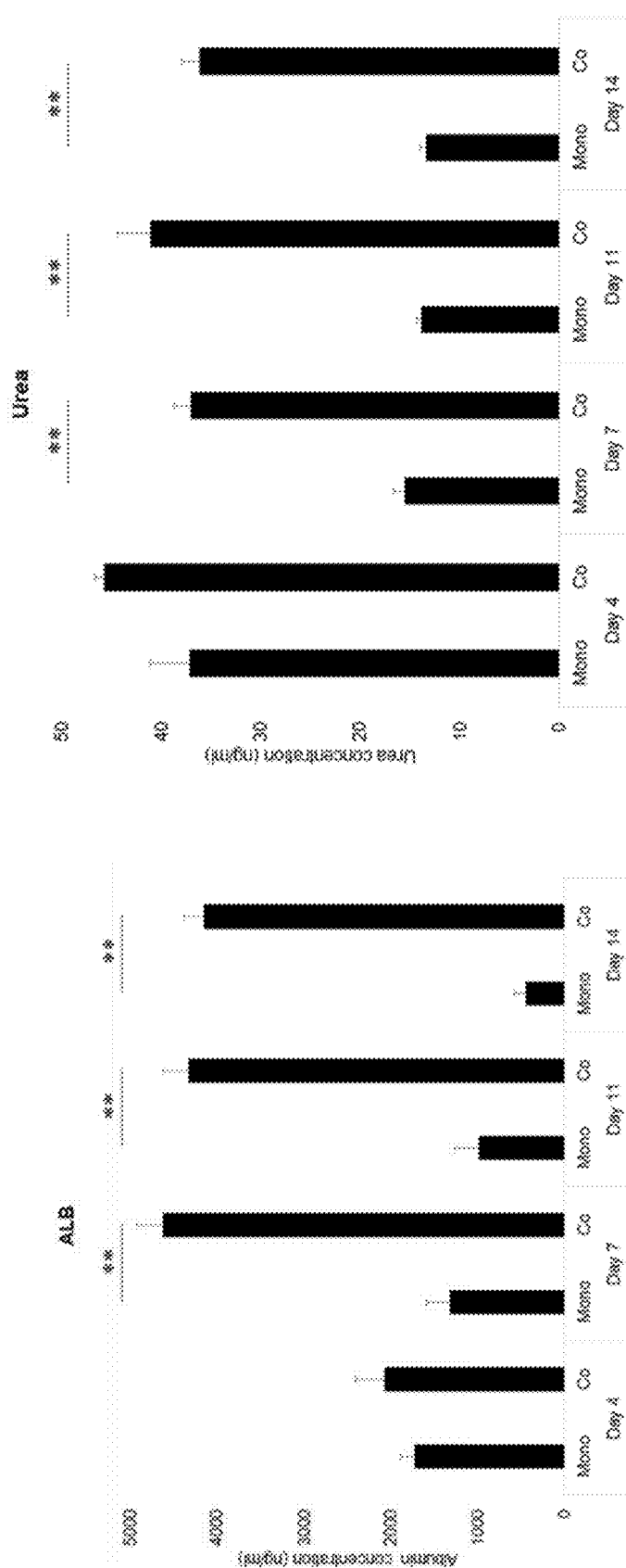
FIG. 6 shows secretion of albumin (ALB) and urea measured by ELISA over 2 weeks of hepatocyte culture. The levels of secreted albumin and urea were significantly higher from hepatocytes in co-culture compared to mono-culture. Mono, mono-culture; Co, Co-culture; *, $p<0.05$; **, $p<0.01$.

The co-cultured hepatocytes secreted significantly higher levels of albumin and urea compared to mono-cultured hepatocytes over 2 weeks of culture as measured by ELISA (FIG. 6).

Figure 8:
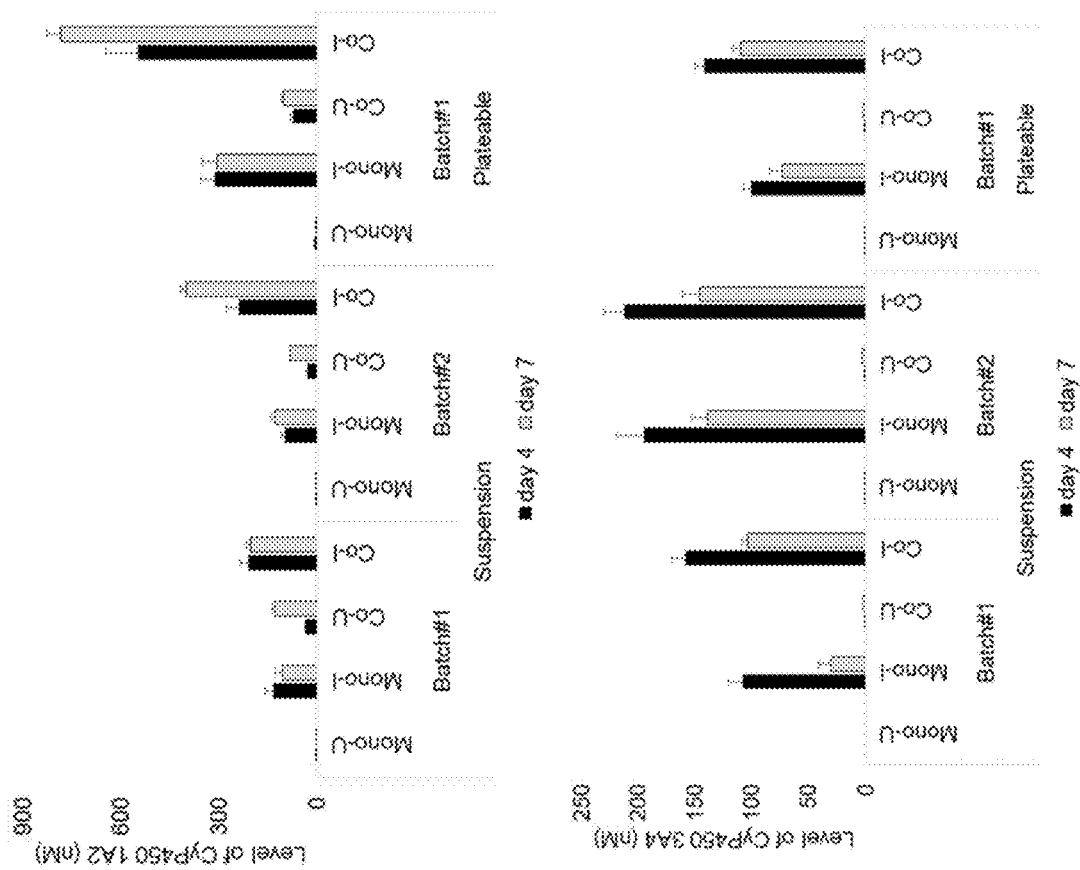
FIG. 8 shows suspension grade hepatocytes in co-culture exhibiting similar or higher expression levels of CyP450 1A2 (top) and CyP450 3A4 (bottom) compared to plateable grade hepatocytes in mono-culture. Both plateable and suspension grade hepatocytes showed higher metabolic activity in co-culture compared to mono-culture. Mono-U, mono-culture uninduced; Mono-I, mono-culture induced; Co-U, co-culture uninduced; Co-I, co-culture induced.
Figure 9:
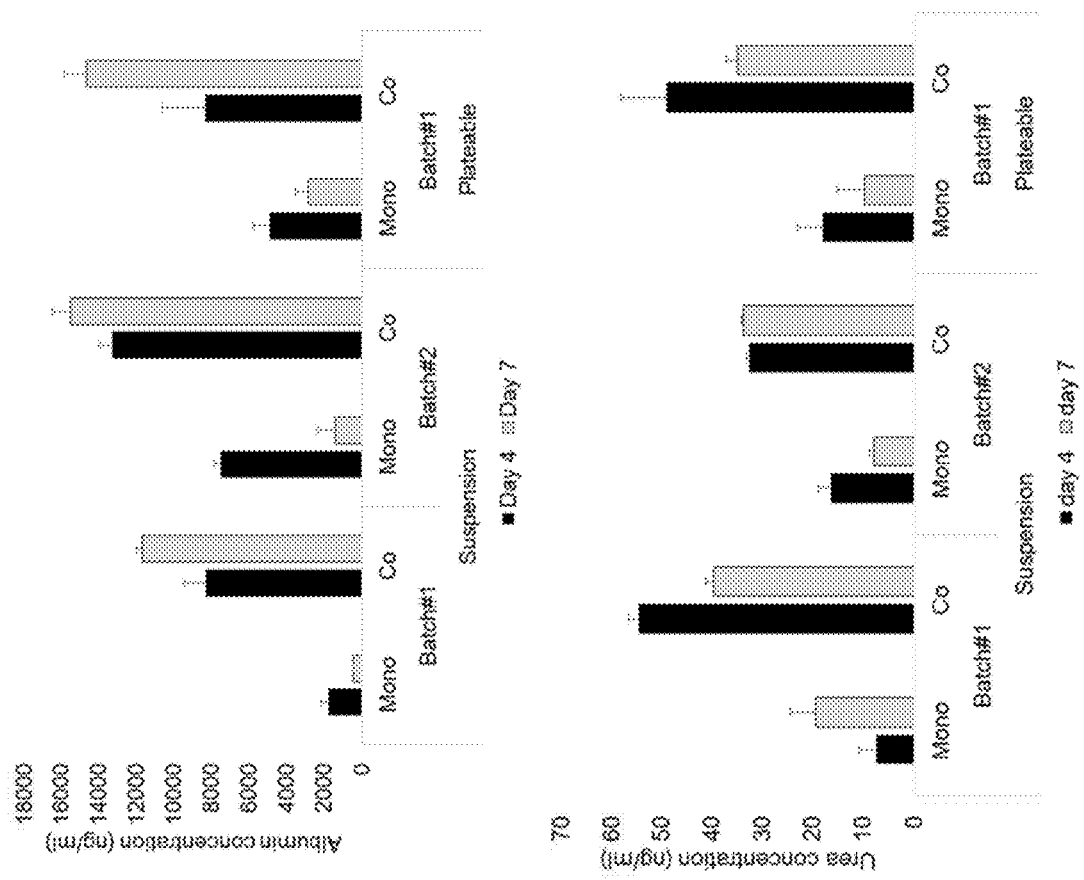
FIG. 9 shows suspension grade hepatocytes in co-culture exhibiting similar or higher secretion levels of albumin (left) and urea (right) compared to plateable grade hepatocytes in mono-culture. Both plateable and suspension grade hepatocytes showed higher functional albumin and urea secretion in co-culture compared to mono-culture. Mono-U, mono-culture uninduced; Mono-I, mono-culture induced; Co-U, co-culture uninduced; Co-I, co-culture induced.

4. Improved Performance of Co-Cultured Suspension Grade Human Primary Hepatocytes vs Mono-Cultured Plateable Grade Hepatocytes Hepatocytes characterized as a suspension grade are unable to sustain a confluent monolayer for multiple days. Adjusting for the donor's attachment rate with the addition of more cells does not improve the attachment and confluence of the hepatocytes. Even if more hepatocytes are seeded to adjust for the specific donor's attachment rate, it is believed that the additional debris will prevent the cells from attaching. This inability of the suspension grade hepatocytes to attach prevents display of typical hepatocyte morphology or function. The addition of a feeder cell layer consisting fibroblasts and endothelial cells in a hepatocyte co-culture improved the attachment, morphology, and functionality of the suspension grade hepatocytes (FIGS. 7-9).

Figure 7:
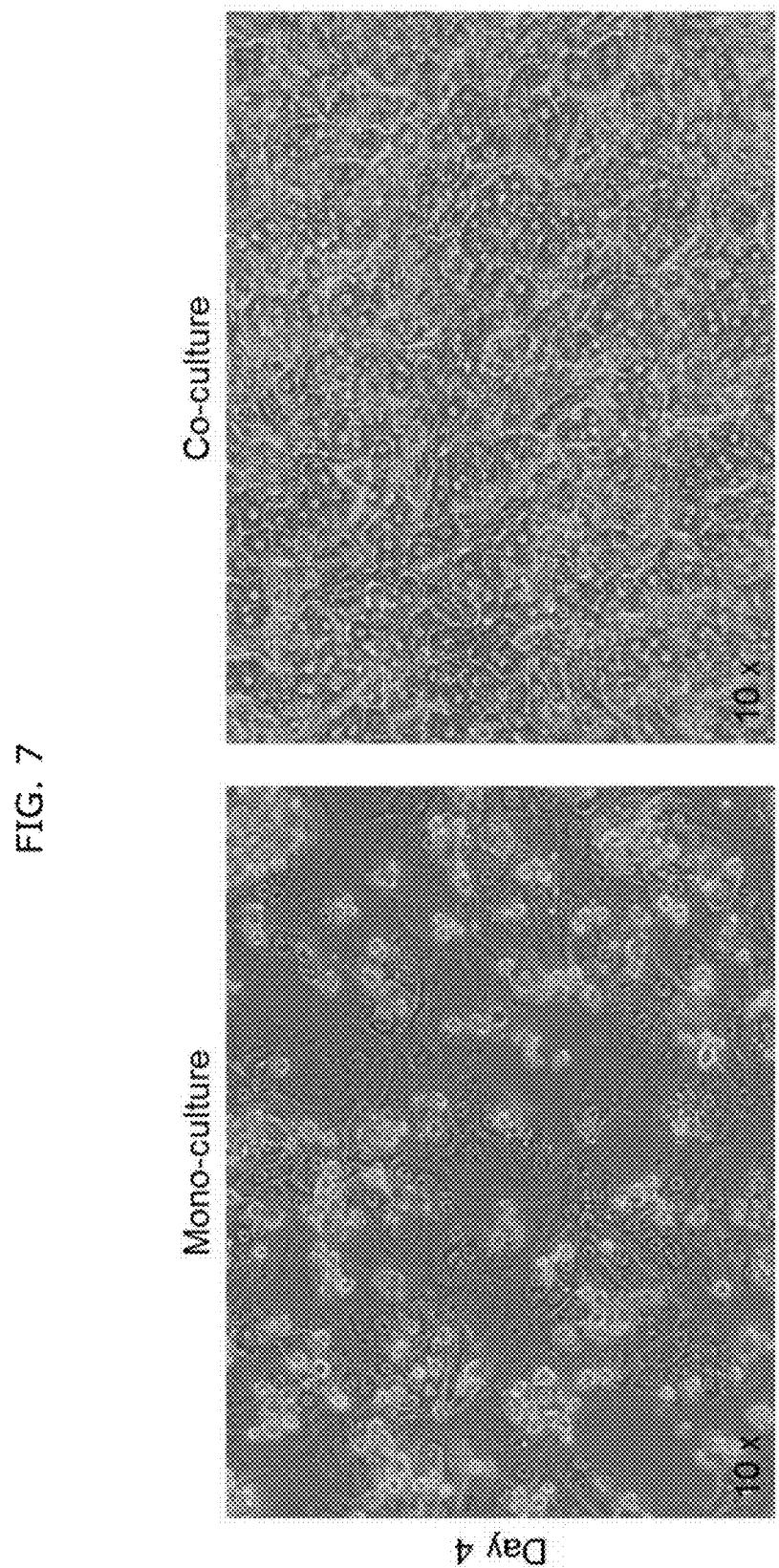
FIG. 7 shows microscopic observation of suspension grade human primary hepatocytes in mono-culture (left) or co-culture with endothelial cells and fibroblasts (right). Hepatocytes in mono-culture started to detach from the day after seeding while the majority of hepatocytes plated in co-culture remained attached in good quality.

The majority of the co-cultured suspension grade human primary hepatocytes remained adherent whereas the majority of the mono-cultured suspension grade human primary hepatocytes never adhered to or detached from a surface by day 4 (FIG. 7).

The co-cultured hepatocytes also showed improvements in cellular function over the mono-cultured hepatocytes. Co-cultured suspension grade hepatocytes showed improved CyP450 1A2 activity and CyP450 3A4 activity over the mono-cultured suspension grade hepatocytes on days 4 and 7, and maintained at higher levels through day 7. The CyP450 1A2 activity of the co-cultured suspension grade hepatocytes was similar to that of mono-cultured plateable grade hepatocytes on days 4 and 7. The CyP450 3A4 activity of the co-cultured suspension grade hepatocytes was greater than that of the plateable grade hepatocytes on days 4 and 7 (FIG. 8). Co-cultured suspension grade hepatocytes and the plateable grade hepatocytes showed higher and sustained albumin and urea expression than the mono-cultured suspension grade hepatocytes and the plateable grade hepatocytes as detected by ELISA. The co-cultured suspension grade hepatocytes showed higher albumin and urea expression than the mono-cultured plateable grade hepatocytes on days 4 and 7 (FIG. 9).

Figure 10:
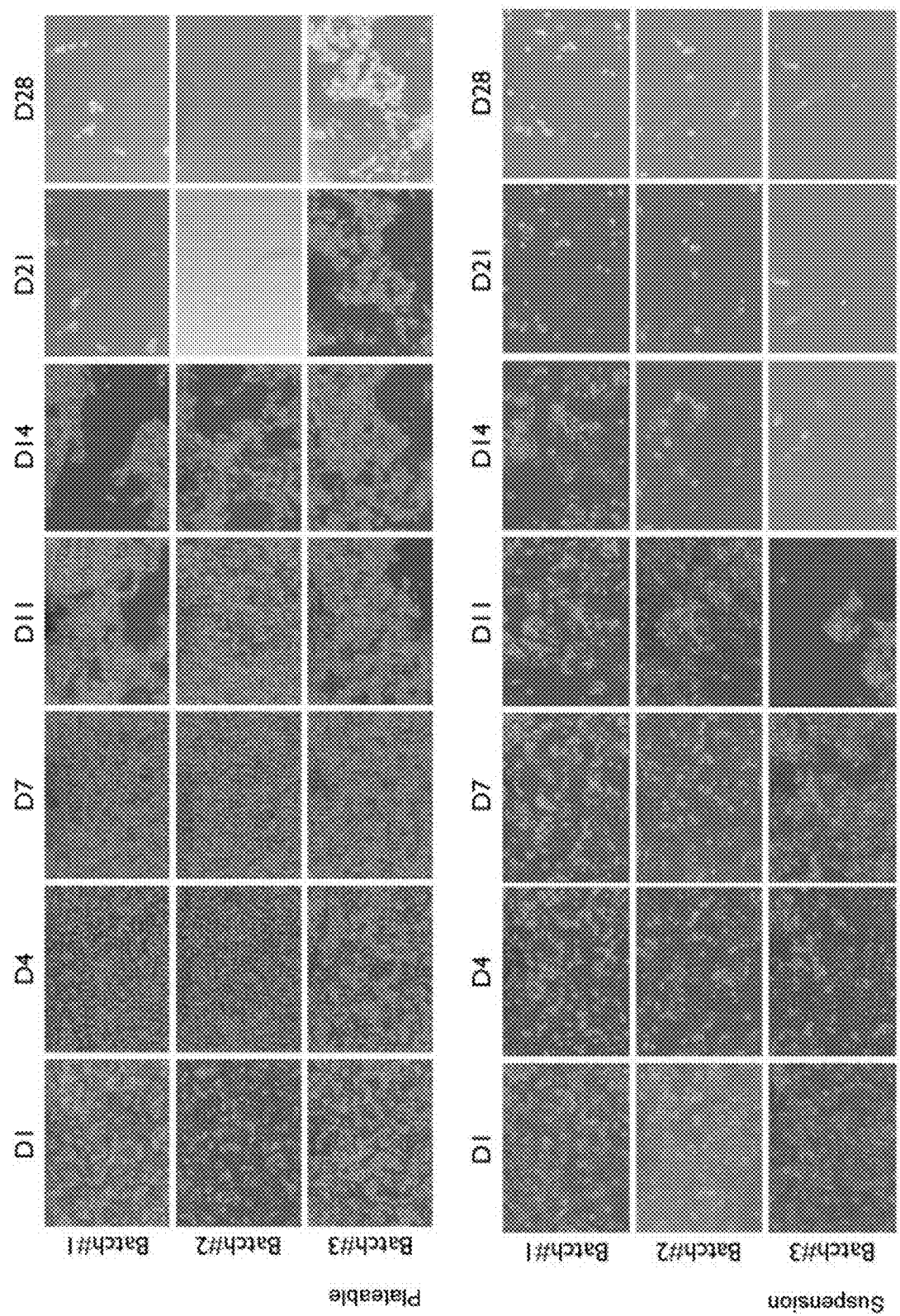
FIG. 10 shows human primary hepatocytes maintained for approximately 7 days of culture under conventional sandwich culture condition (mono-culture). Six batches of hepatocytes, including three batches of plateable grade hepatocytes and three batches of suspension grade hepatocytes, were observed over 4 weeks of culture. The majority of the hepatocytes detached around day 7 of culture.

5. Longevity of Co-Cultured Hepatocytes Morphology, Marker Expression, Metabolic Activity and Functional Bile, Secretion The majority of mono-cultured suspension grade human primary hepatocytes did not attach to a surface, and those that did attach to a surface began to detach from the surface after a maximum of one week in culture. The plateable grade hepatocytes initially attached to a surface at a high efficiency, but began to detach from the surface and lose their cuboidal morphology by day 7 of culture. The plateable hepatocytes did not remain attached for more than 11 days of culture (FIG. 10).

Figure 11:
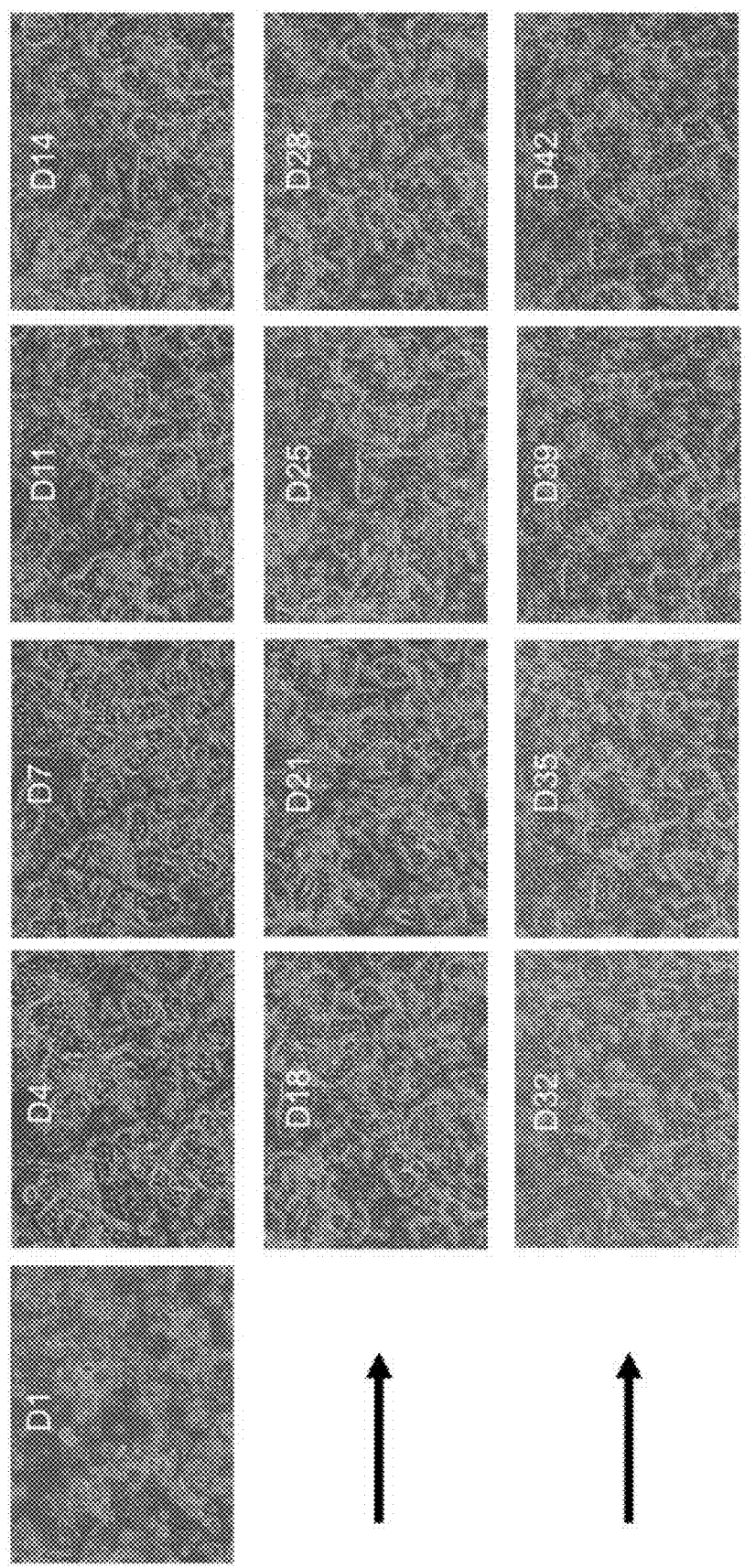
FIG. 11 shows hepatocytes plated onto a mixture of endothelial cells and fibroblasts in co-culture maintained up to 6 weeks. 10× magnification.
Figure 12:
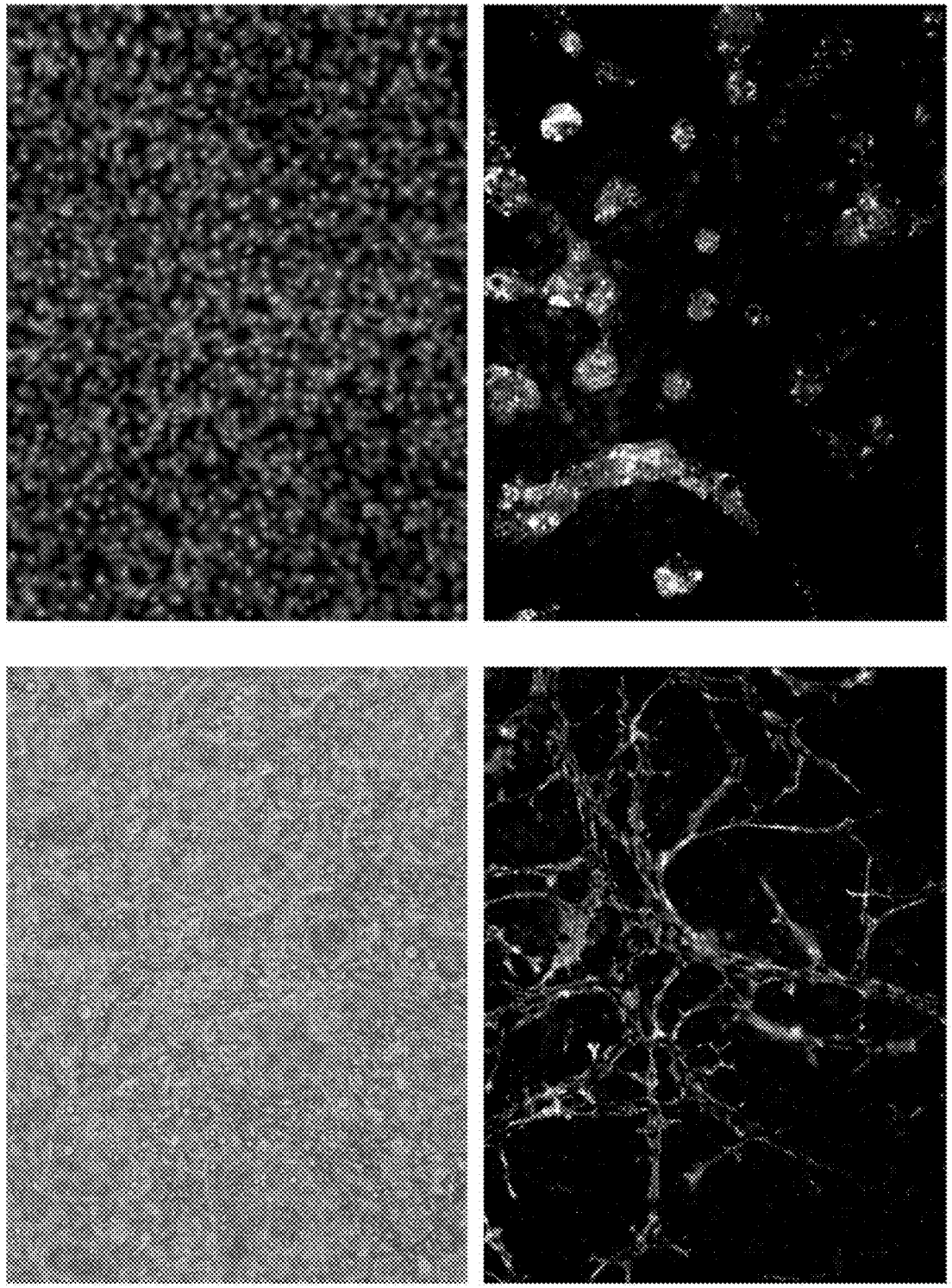
FIG. 12 shows immunocytochemical staining of hepatocytes 43 days in co-culture after plating. Staining of albumin (bottom right) and CD31 (bottom left) indicated geographical distribution of hepatocytes, endothelial cells and fibroblasts. 10× magnification.
Figure 13:
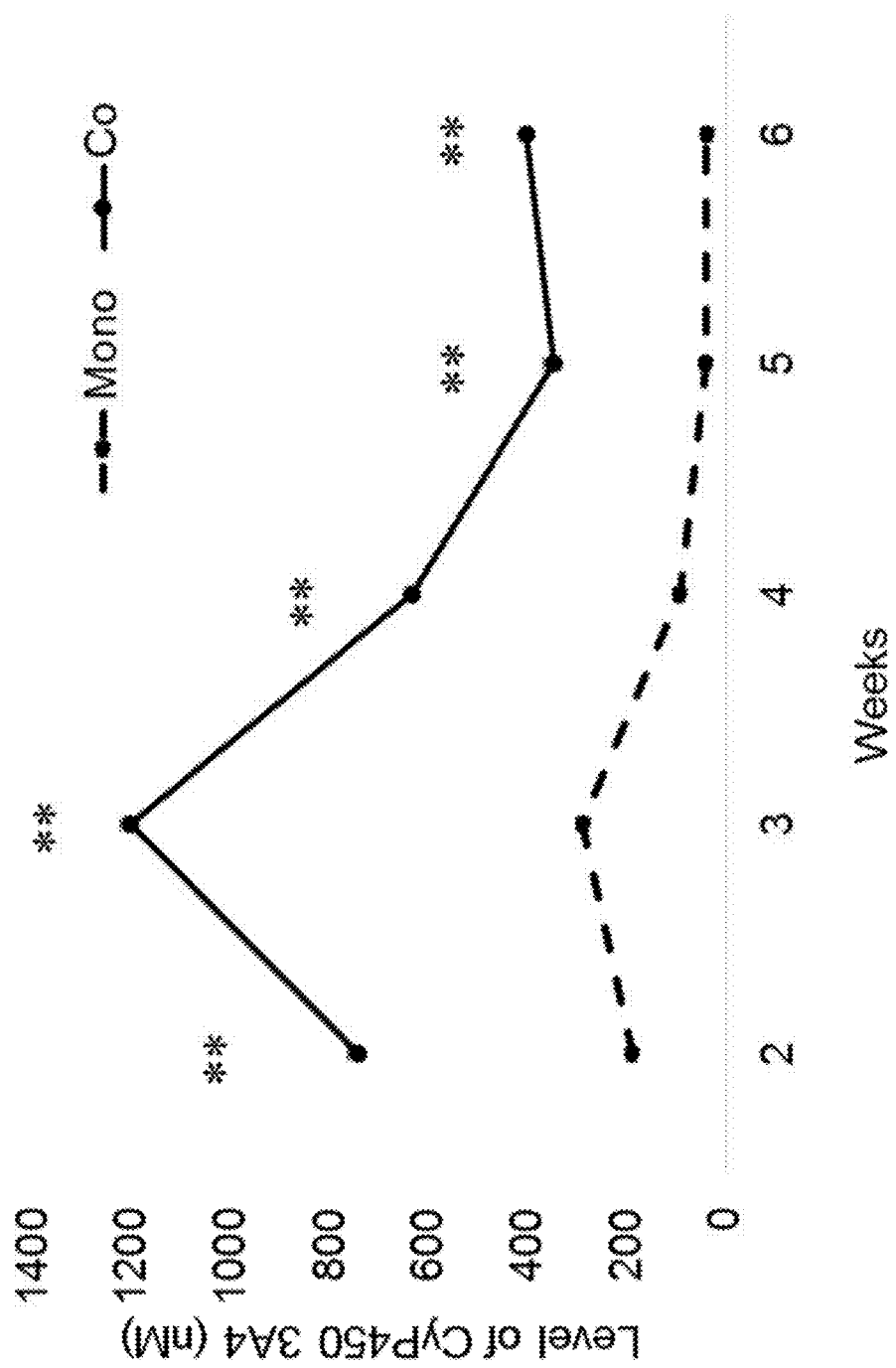
FIG. 13 shows hepatocytes exhibiting higher activity level of CyP450 3A4 in co-culture compared to those in mono-culture over 6 weeks of culture. The activity level of CyP450 3A4 was peaked at week 3 and sustained metabolic activity for 6 weeks in co-culture whereas that in mono-culture discontinued metabolic activity. **, $p<0.01$.
Figure 14:
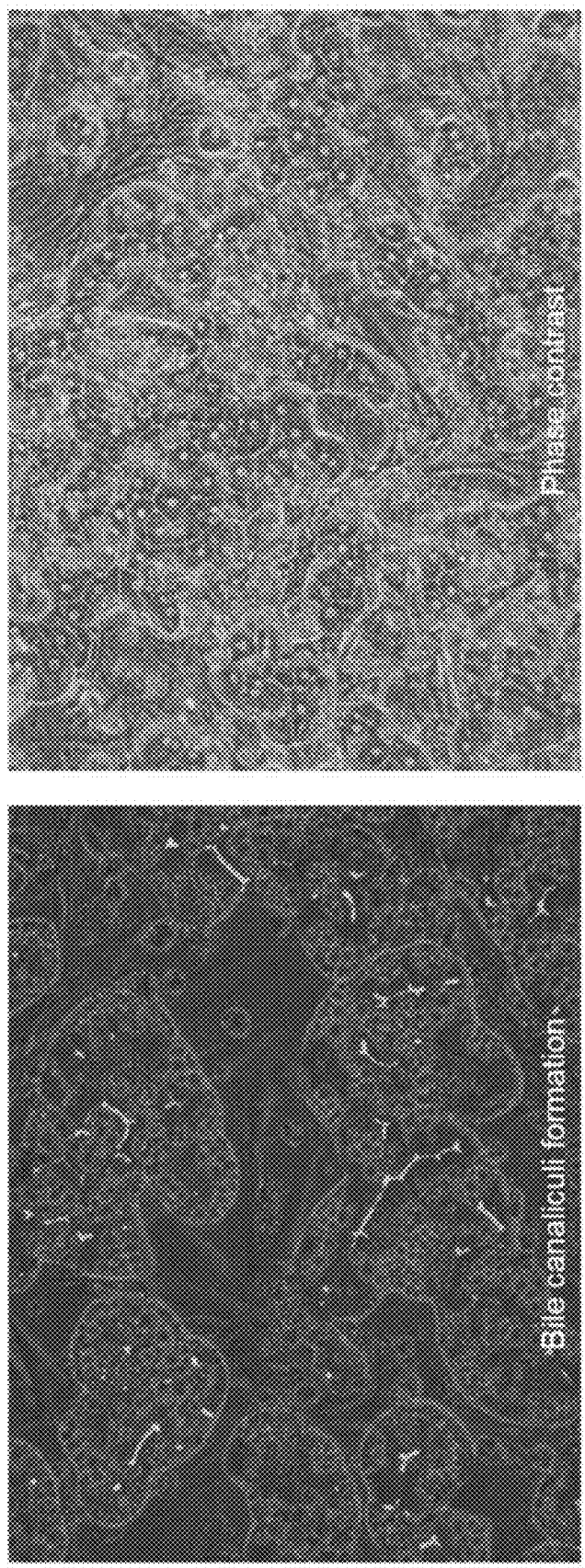
FIG. 14 shows functional bile secretion from human hepatocytes in co-culture observed by imaging FITC conjugated CDFDA efflux to bile canaliculi. 10× magnification.

Co-cultured suspension grade hepatocytes were maintained for 6 weeks or longer. The cuboidal hepatocyte morphology was clearly maintained as the hepatocytes that remained attached in compact islands on a non-proliferating feeder layer of fibroblasts and endothelial cells for 6 weeks (FIG. 11). Longer time points were not tested. The interactions between the hepatocytes and the feeder cells were visualized through albumin and CD31 staining. The hepatocytes were integrated into the supporting feeder layer as a complex network of cells. The hepatocyte functions were maintained in this network as visualized by the albumin and CyP450 3A4 staining (FIG. 12). The CyP450 3A4 activity of the co-cultured suspension grade hepatocytes was maintained for 6 weeks. The high activity of the co-cultured suspension grade hepatocytes was in contrast to the low CyP450 3A4 activity of the same hepatocytes cultured as a sandwich monoculture (FIG. 13). The co-cultured suspension grade hepatocytes developed and maintained functional networks of bile canaliculi over the 6 weeks of culture (FIG. 14).

Figure 15:
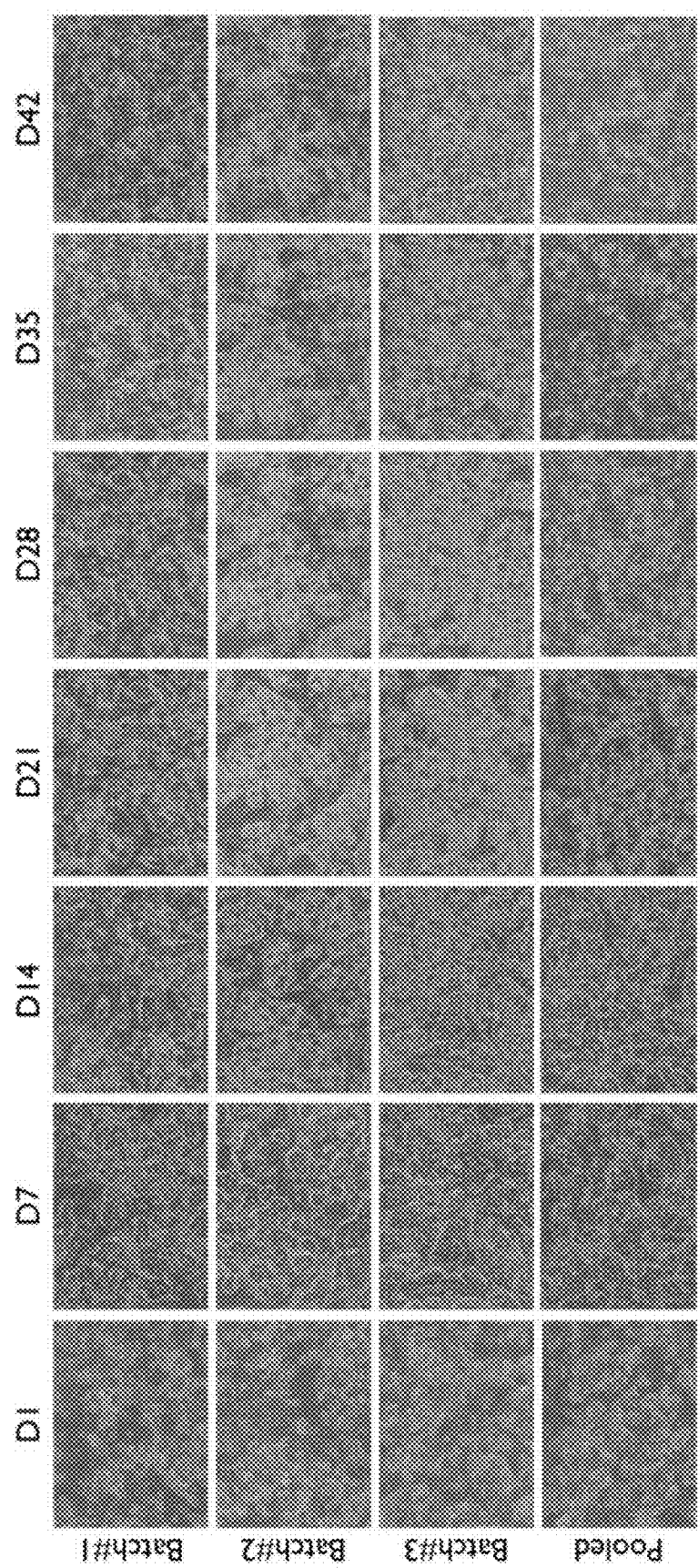
FIG. 15 shows hepatocytes from three separate batches and pooled those 3 batches in co-culture condition maintained up to 6 weeks. Hepatocytes were overlayed with MATRIGEL on next day after seeding on a mixture of endothelial cells and fibroblasts. 10× magnification.
Figure 16:
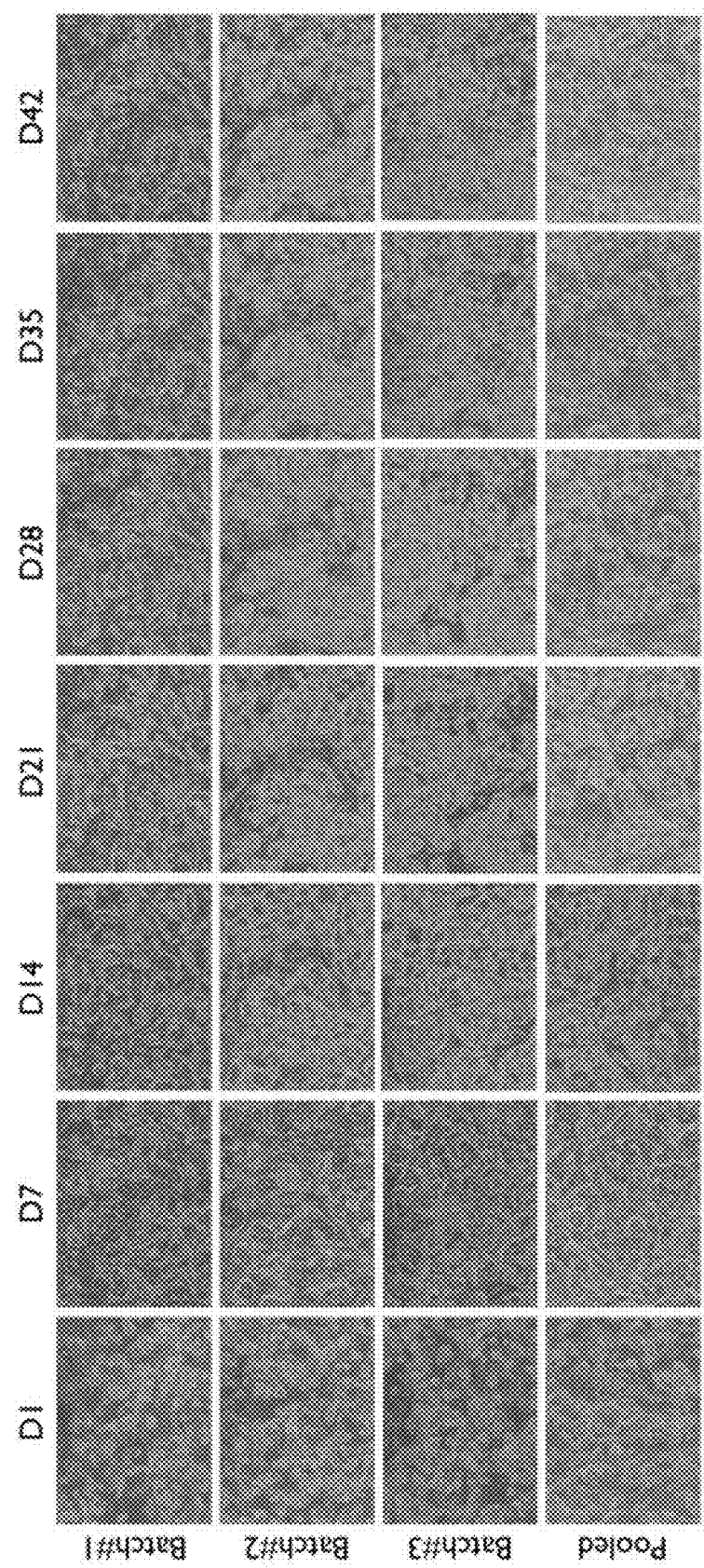
FIG. 16 shows that hepatocytes pooled from three different batches could be maintained up to 6 weeks in in co-culture. Hepatocytes were cultured without overlayed MATRIGEL on a mixture of endothelial cells and fibroblasts. 10× magnification.
Figure 17:
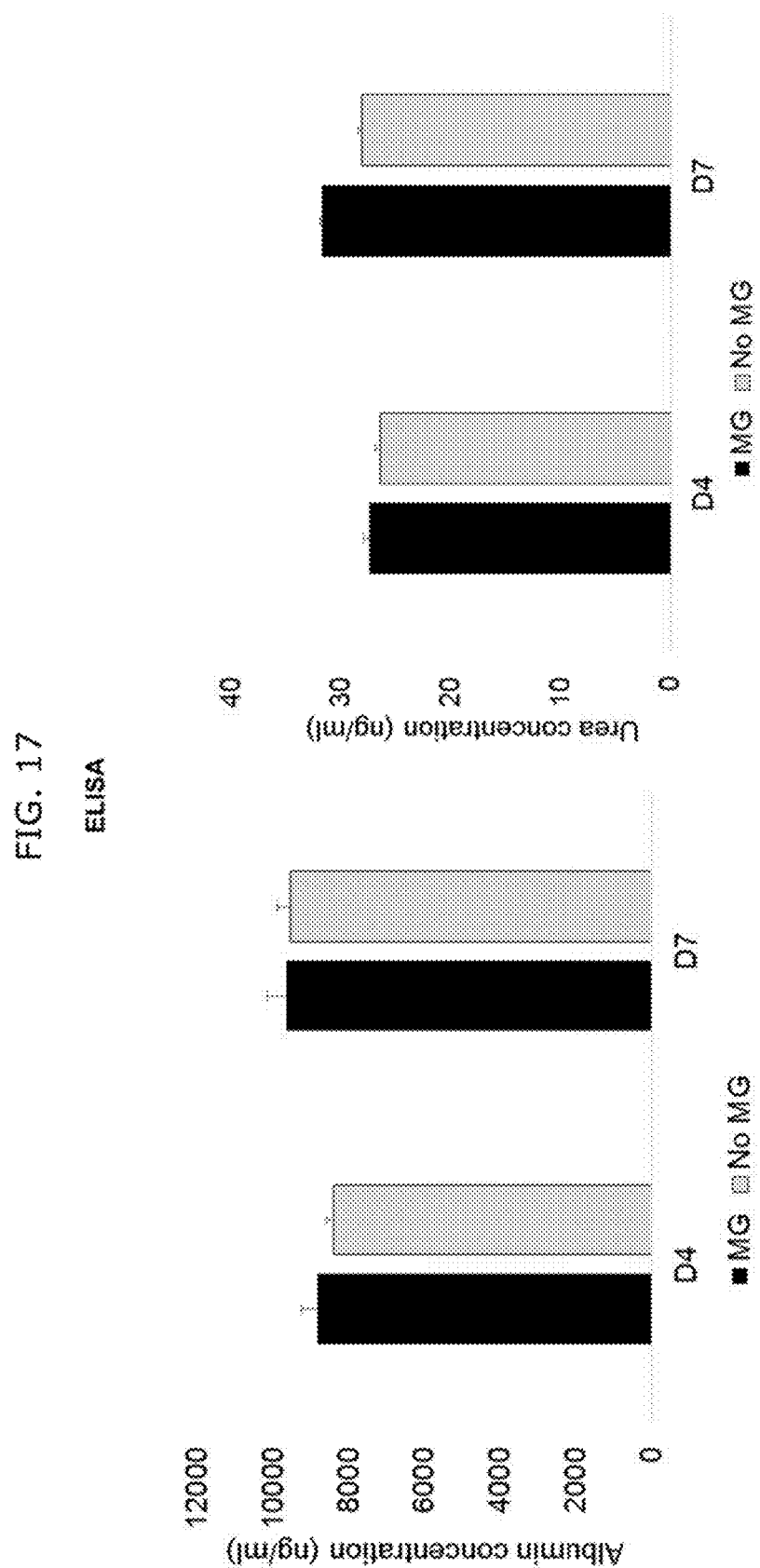
FIG. 17 shows secretion levels of albumin (left) and urea (right) from hepatocytes in co-culture without tapping MATRIGEL was similar to hepatocytes in co-cultured with MATRIGEL tapping. MG, MATRIGEL tapped; No MG, Non MATRIGEL tapped; D4, day 4; D7, day 7.
Figure 18:
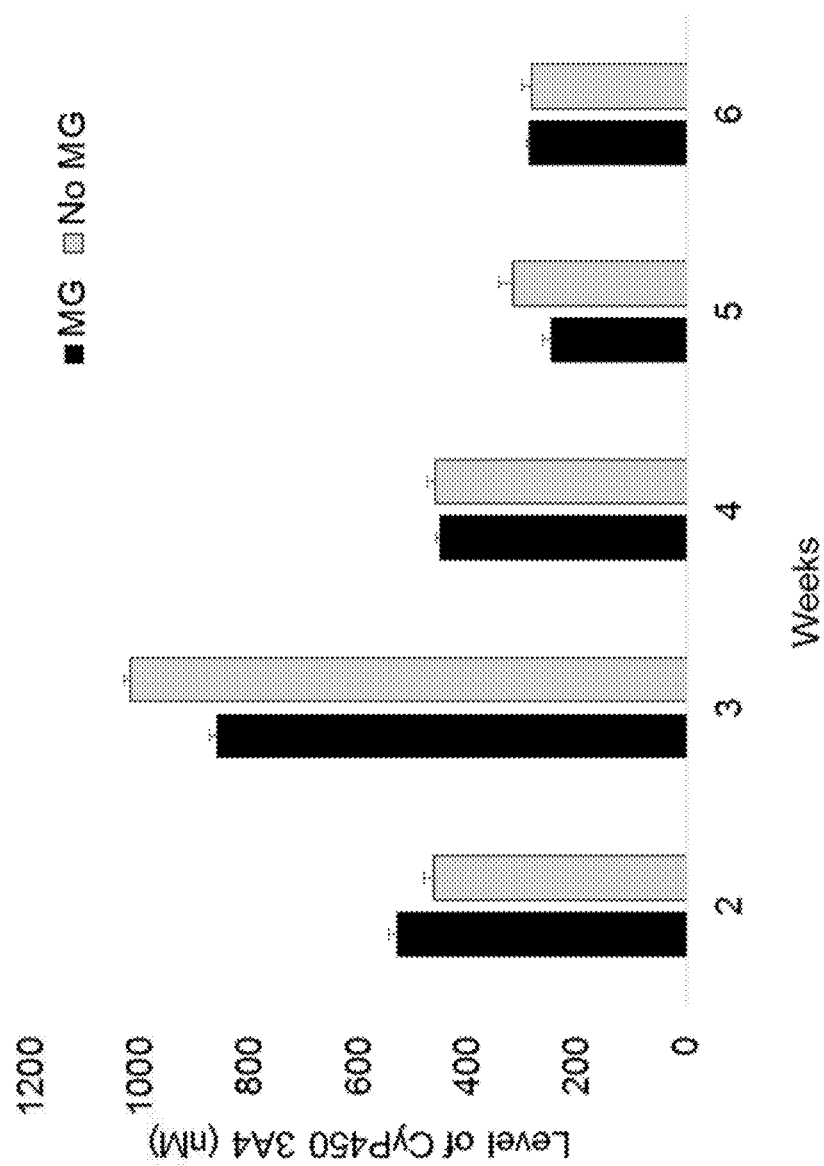
FIG. 18 shows expression levels of CyP450 3A4 from hepatocytes in co-culture without tapping MATRIGEL similar to hepatocytes in co-cultured with MATRIGEL tapping up to 6 weeks. MG. MATRIGEL tapped; No MG, Non MATRIGEL tapped.

6. Longevity of Co-Cultured Hepatocytes: Maturation Induction of Hepatocytes in Co-Culture in the Presence or Absence of MATRIGEL Co-cultured hepatocytes did not need MATRIGEL or any other extracellular matrix to maintain their morphology, function or longevity. The morphology of the co-cultured suspension grade hepatocytes with and without MATRIGEL was remarkably similar throughout weeks 1 through 6 (FIGS. 15 and 16). The Hepatocytes, with and without MATRIGEL, formed compact islands of cells and networks with their feeder layers. The interactions between the feeder cells and the hepatocytes were visualized through ICC after 6 weeks of culture and the bile canaliculi observed throughout the six weeks (data not shown). No morphology difference was observed in the hepatocytes cultured with or without MATRIGEL. The presence of MATRIGEL did not affect the functionality of the co-cultured hepatocytes. Albumin and urea concentrations as well as CyP450 3A4 activity remained constant over the 6 weeks of culture for the co-cultured hepatocytes with and without MATRIGEL (FIGS. 17 and 18).

Figure 19:
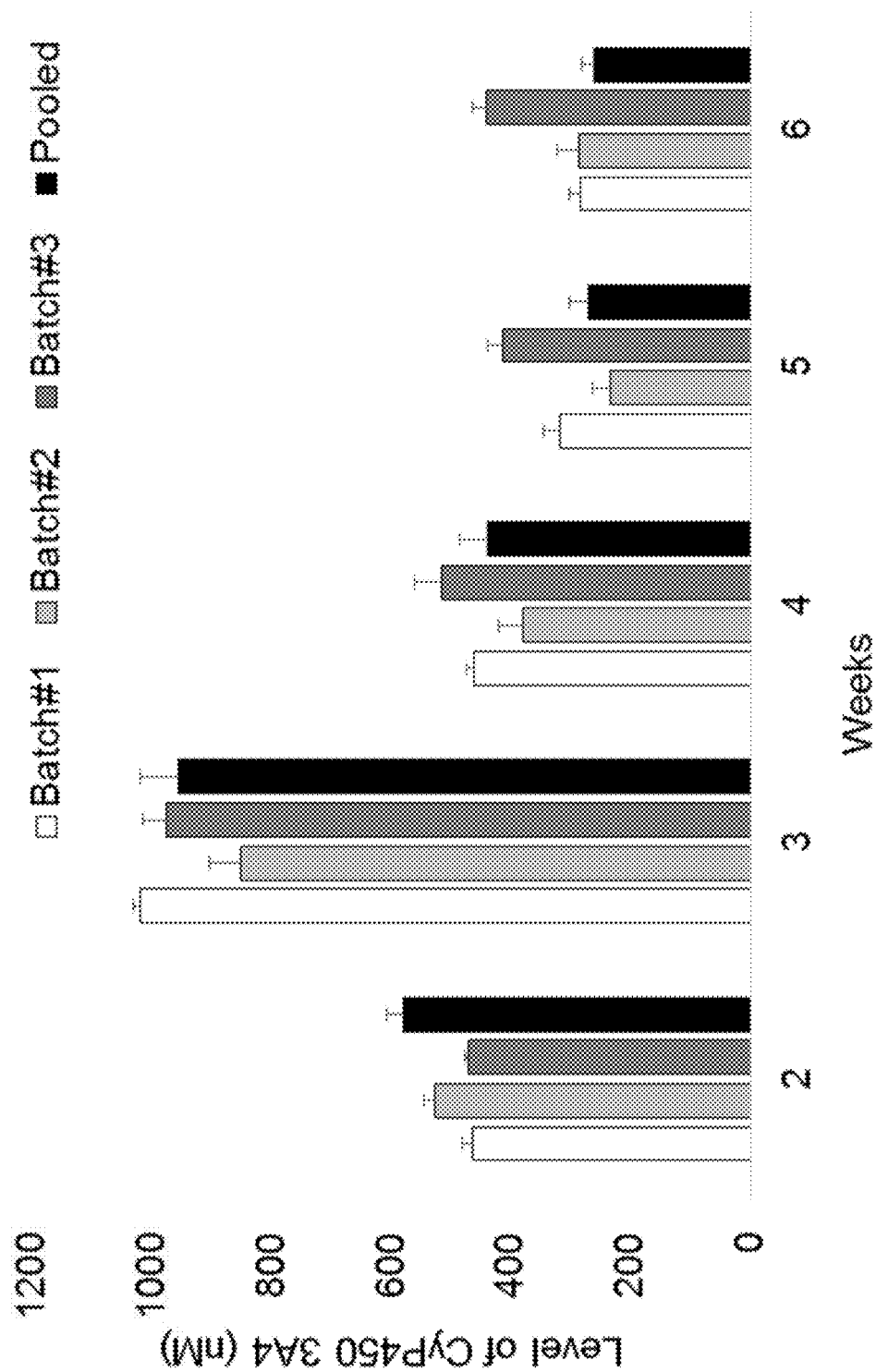
FIG. 19 shows metabolic activity measured by CyP450 3A4 from three different batches of human primary hepatocytes similar to that of pooled hepatocytes from the three different batches in co-culture up to 6 weeks.

Mono-cultured and co-cultured hepatocytes from different donors showed significant variations in morphology, protein expression, and enzyme activity. Hepatocytes from multiple donors could be pooled together to normalize these variations. The attachment rate, confluency, and lipid accumulation of pooled hepatocytes from three donors in the co-culture system appeared to be normalized (FIGS. 15 and 16). The CyP450 3A4 enzyme activity of the pooled hepatocytes appeared to be an average or slightly higher than the average when compared to hepatocytes from individual donors (FIG. 19). The normalization effect of pooling hepatocytes from three or more donors is useful for in vitro testing applications.

Figure 20:
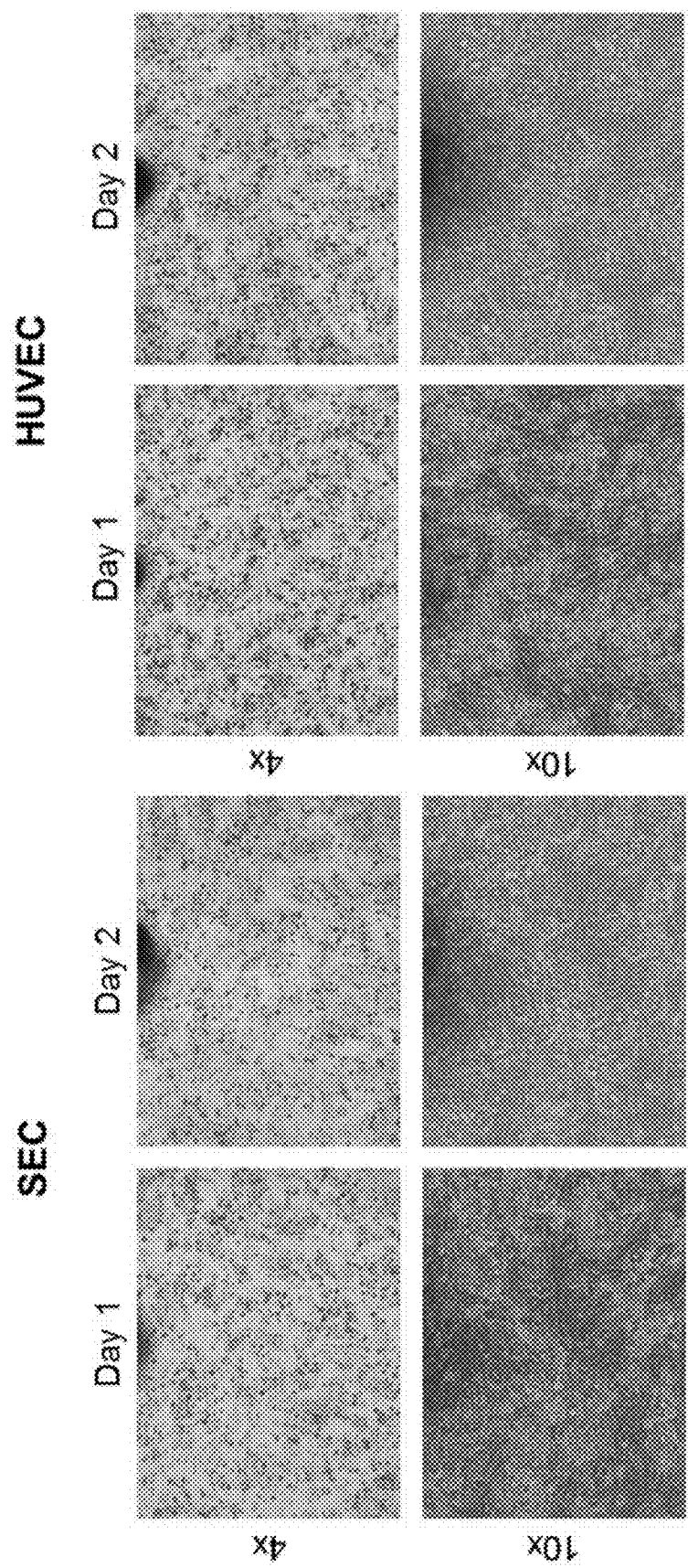
FIG. 20 shows that endothelial cells of different sources support a hepatocyte culture. Both immortalized liver sinusoidal endothelial cells (SECs) and human umbilical vein endothelial cells (HUVECs) could support a hepatocyte culture.
Figure 21:
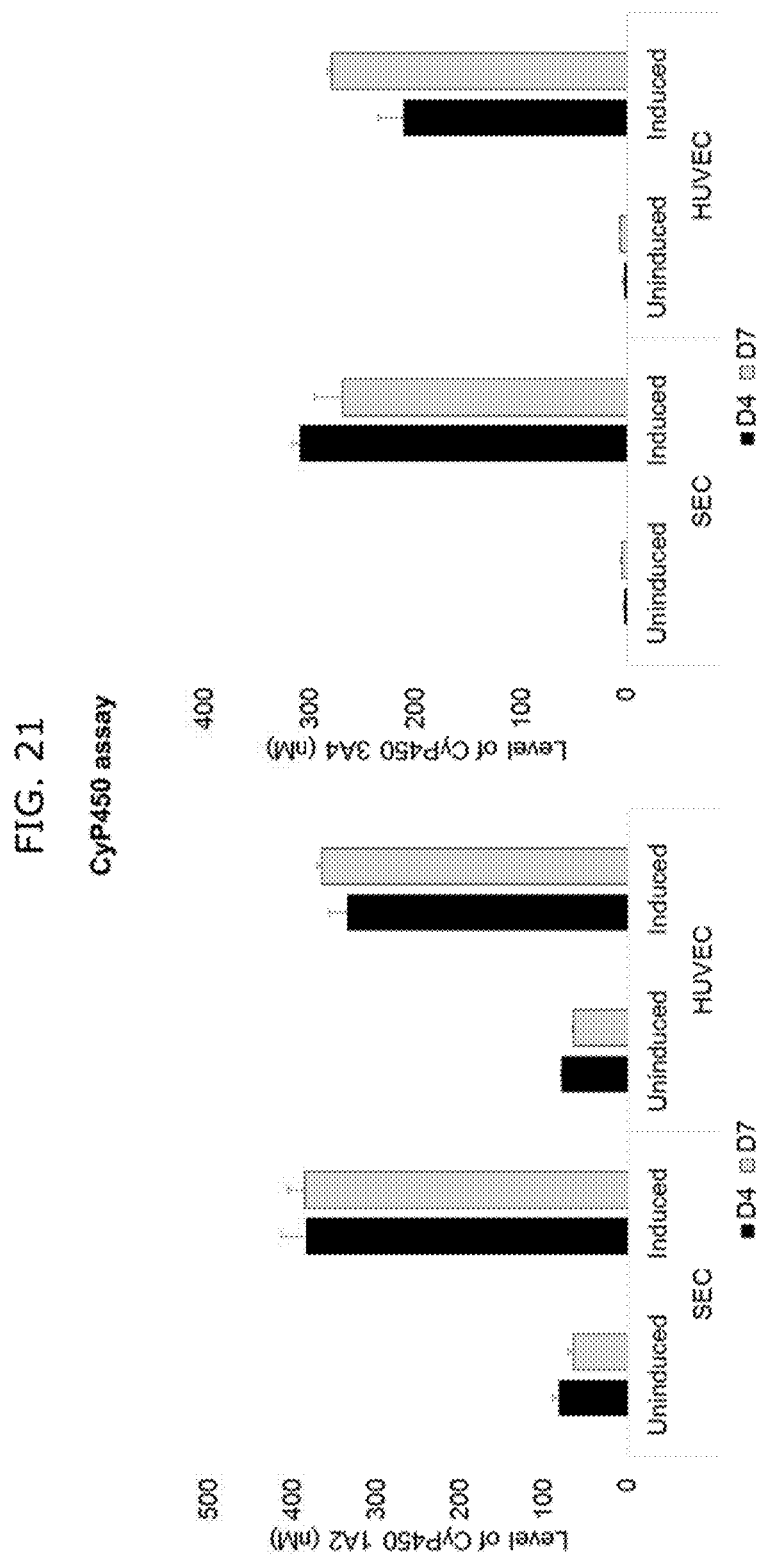
FIG. 21 shows similar expression levels of CyP450 1A2 and CyP450 3A4 by hepatocytes co-cultured on immortalized liver sinusoidal endothelial cells (SECs) or human umbilical vein endothelial cells (HUVECs). D4, day 4; D7, day 7.
Figure 22:
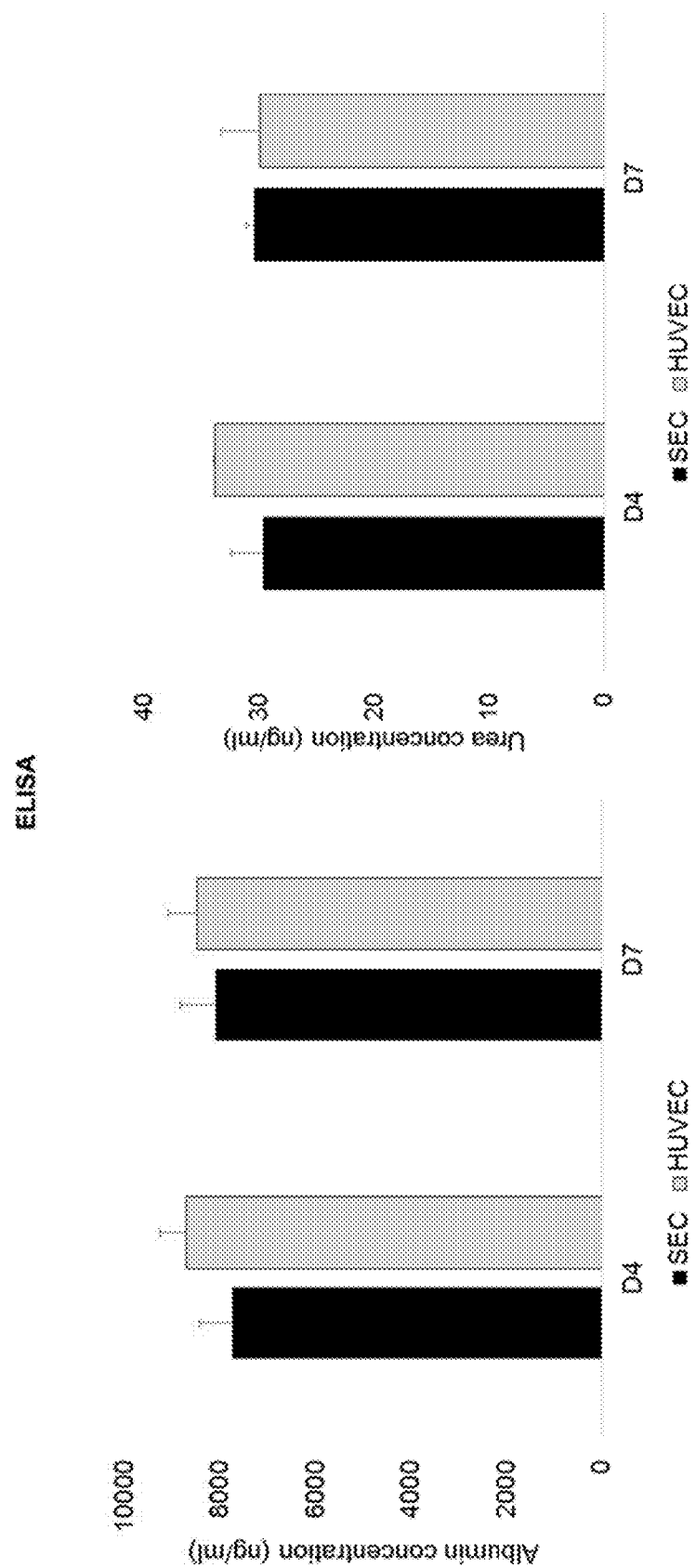
FIG. 22 shows similar levels of albumin and urea secretion by hepatocytes co-cultured on immortalized liver sinusoidal endothelial cells (SECs) or human umbilical vein endothelial cells (HUVECs) showed. D4, day 4; D7, day 7.

The feeder layer may consist of multiple types of endothelial cells and fibroblasts. The morphology and function of co-cultured human hepatocytes on a feeder cell layer containing sinusoidal endothelial cells or HUVECs were compared. No significant difference was observed in morphology (FIG. 20), CyP450 activity (FIG. 21), or secretion of albumin and urea (FIG. 22).

7. Optimal Ratio of Cellular Mixture for Co-Cultured Hepatocytes

Figure 23:
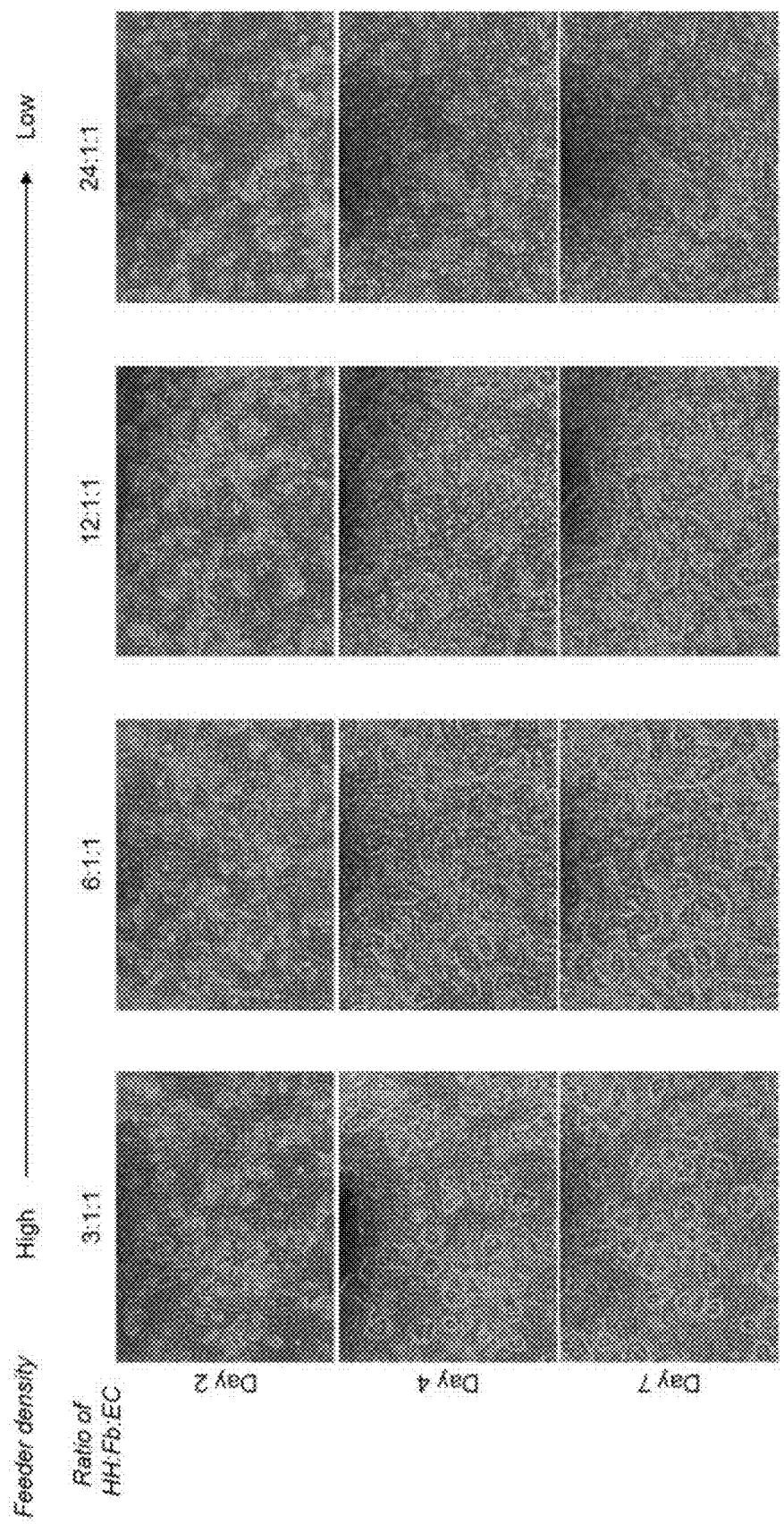
FIG. 23 shows morphology of hepatocytes in co-culture at different cell ratios. HH, human hepatocyte; Fb, fibroblast; EC, endothelial cell.
Figure 24:
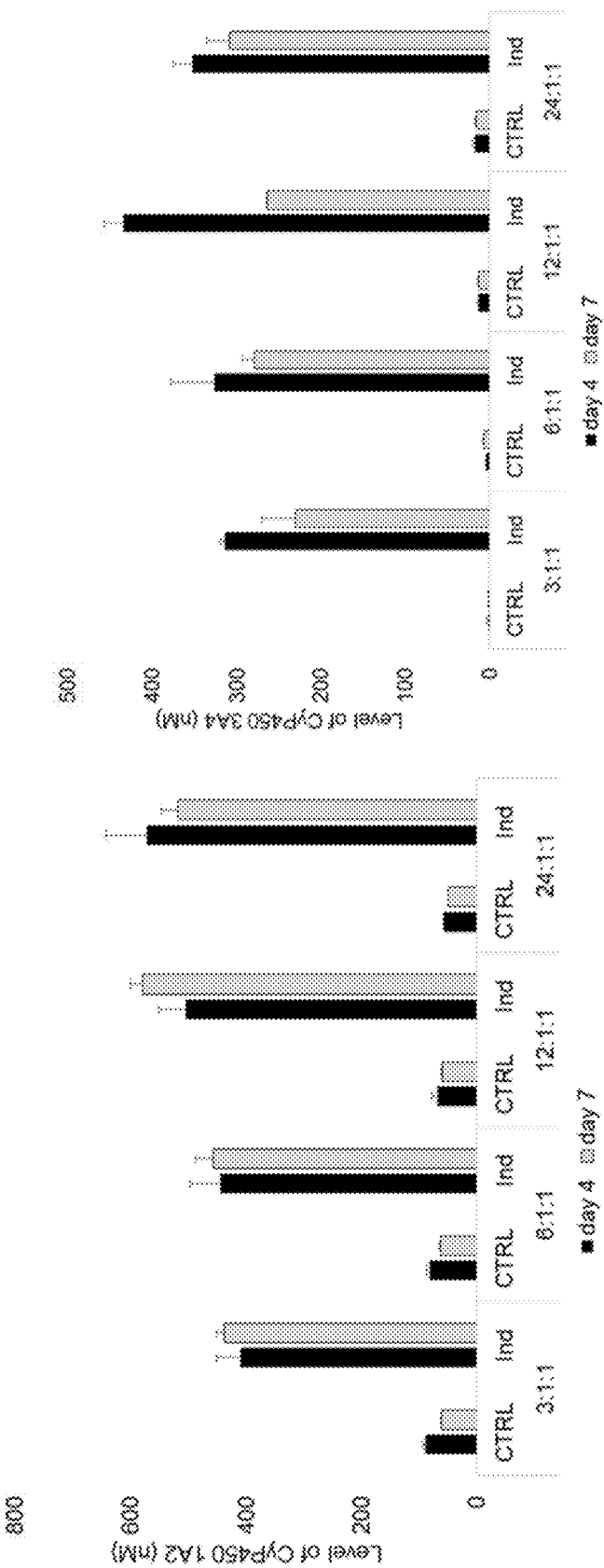
FIG. 24 shows expression levels of CyP450 1A2 and CyP450 3A4 by hepatocytes co-cultured with endothelial cells and fibroblasts at different ratios. The cellular mixture of hepatocyte, endothelial cells, and fibroblasts at 12:1:1 showed highest expression levels of CyP450 1A2 and CyP450 3A4 compared to those at other ratios. CTRL, uninduced control; Ind, Induced.

Feeder layer densities from 12,500 cells/cm$^2$ to 100,000 cells/cm$^2$ were tested in a co-culture system. Although the individual hepatocyte morphology on different feeder cell densities appeared similar, lower densities of feeder cells allowed for more hepatocyte-to-hepatocyte interaction (FIG. 23). The co-cultured hepatocytes showed higher CyP450 1A2 activity and CyP450 3A4 activity at a feeder cell density of 12,500 cells/cm$^2$ (24:1:1) or 25,000 cells/cm$^2$ (12:1:1) than those at a higher density of 50,000 cells/cm$^2$ (6:1:1) or 100,000 cells/cm$^2$ (3:1:1) (FIG. 24).

8. Multiple Types of Culture Plates for Hepatocyte Co-Culture

Hepatocytes co-cultured on endothelial cells and fibroblasts in either 24- or 96-well plates showed similar features such as morphology (FIG. 25, left and center panels), level of albumin secretion (FIG. 26), and biomarker expression (FIG. 27). Hepatocytes co-cultured on general tissue culture plastic without collagen-coating showed similar morphology (FIG. 25, right panel) and biomarker expression pattern (FIG. 27) compared to co-cultured hepatocytes on collagen-coated BioCoat plate.

Even though only suspension grade hepatocytes were co-cultured so far, it is expected that the plateable grade hepatocytes will maintain a similar high grade morphology and function for 6 weeks or longer. It is anticipated that higher grade cells may even develop more complex networks with each other and with the feeder cells more quickly.

Example 2

HBV Infection Model (NTCP Expression)

Figure 25:
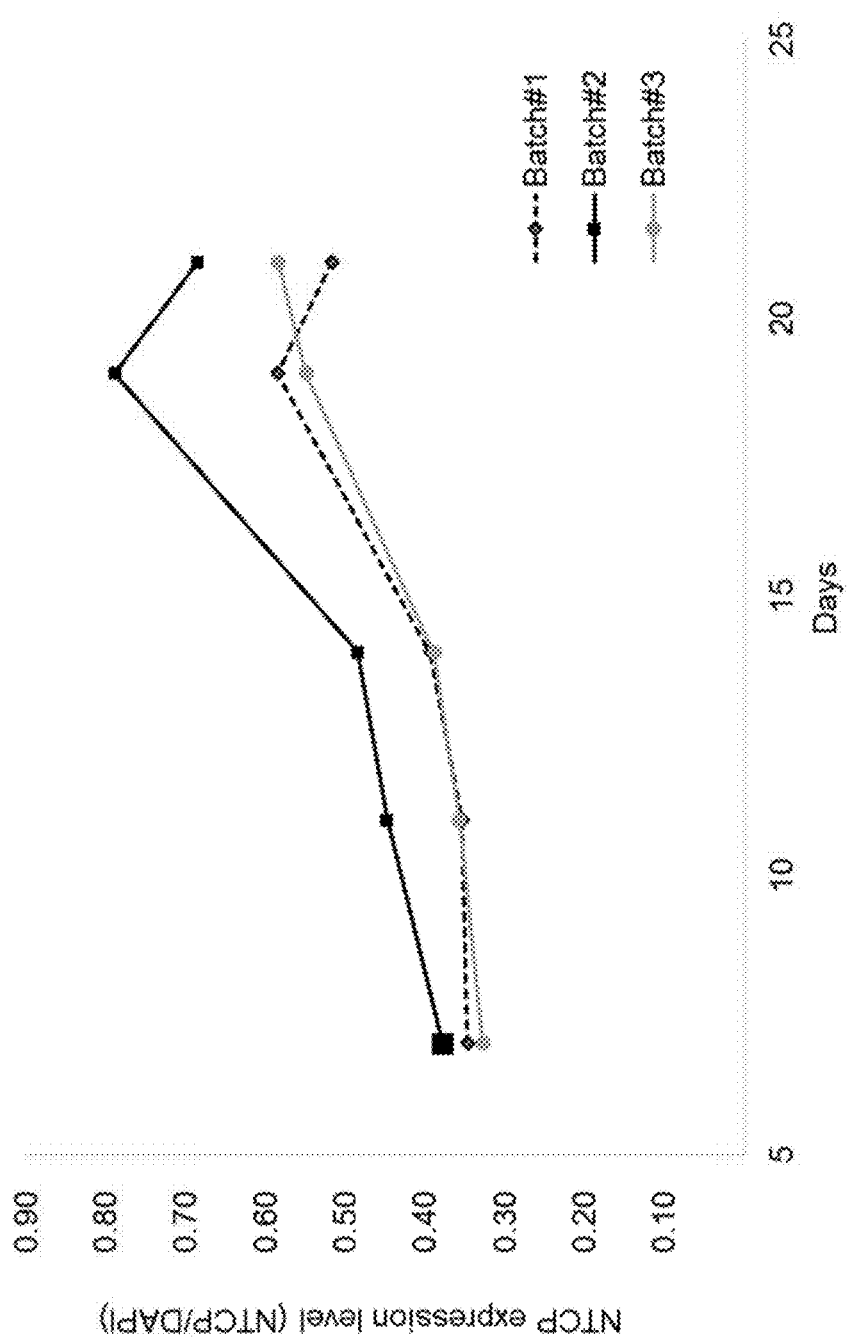
FIG. 25 shows expression level of sodium taurocholate cotransporting polypeptide (NTCP) as a cellular receptor for hepatitis B virus (HBV) on co-cultured hepatocytes in multiple time points.

NTCP (sodium/taurocholate cotransporting polypeptide) expression is necessary for the uptake of HBV by hepatocytes. Co-cultured hepatocytes were found to express NTCP on days 7, 11, 14, 19, and 21 detected with immunocytochemistry. Cells were fixed, permeabilized, and incubated with primary antibody SLC10A1 (abeam 131084) at a concentration of 1:100 at 4° C. overnight. Secondary antibody Alexa Fluor 488 goat anti rabbit (Invitrogen A11008) was incubated at a concentration of 1:1000 at 4 C for one hour to detect the primary antibody. Cells were counter stained with Hoechst. NTCP expression was quantified with whole well fluorescence scanning with a BMG CLARIOstar (FIG. 25). Thus, NTCP expression was sustained by the co-cultured hepatocytes over a three-week period.

Example 3

Optimal Ratios for Cells and Medium

Feeder cell seeding densities of 12,500, 25,000, 50,000, and 100,000 cells per square centimeter were tested for hepatocyte attachment and cluster formation. Hepatocyte seeding densities of 150,000, 250,000, 375,000 cells per square centimeter were tested. Culture media ratios of hepatocyte culture media, endothelial cell media, and fibroblast media were tested for an ideal cellular ratio as well. A feeder cell ratio of 12,500 to 25,000 cells per square centimeter and a hepatocyte seeding density of 150,000 cells per square centimeter showed the highest attachment rate, cluster formation, and hepatocyte function. A medium ratio matching the cellular ratio was also found to maximally support the hepatocyte morphology and function.

Example 4

Hepatocyte Clusters

A layer of feeder cells composed of fibroblasts and endothelial cells attached to a tissue culture plastic surface within the first minutes after the feeder cells were seeded. The feeder cells were seeded at a density sparse enough to allow the feeder cells to spread out, migrate and coat the tissue culture plastic surface. The hepatocytes then attached onto the top of the feeder cells and migrated towards each other forming clusters hepatocytes. This hepatocyte migration occurred within the first hour or up to 48 hours, depending on the characteristics of the hepatocytes. Once the hepatocyte clusters were formed, adjacent hepatocytes formed functional bile canaliculi and tight junctions. Bile canaliculi was visualized through the efflux of CDFDA starting on day 4. Junctional proteins zonal occludin 1 and connexin-32 were visualized on day 7 using immunocytochemistry. At least 90% of the hepatocytes in the clusters showed tight gap junction, indicating direct hepatocyte-hepatocyte contact.

Example 5

Cluster Measurements

Figure 26:
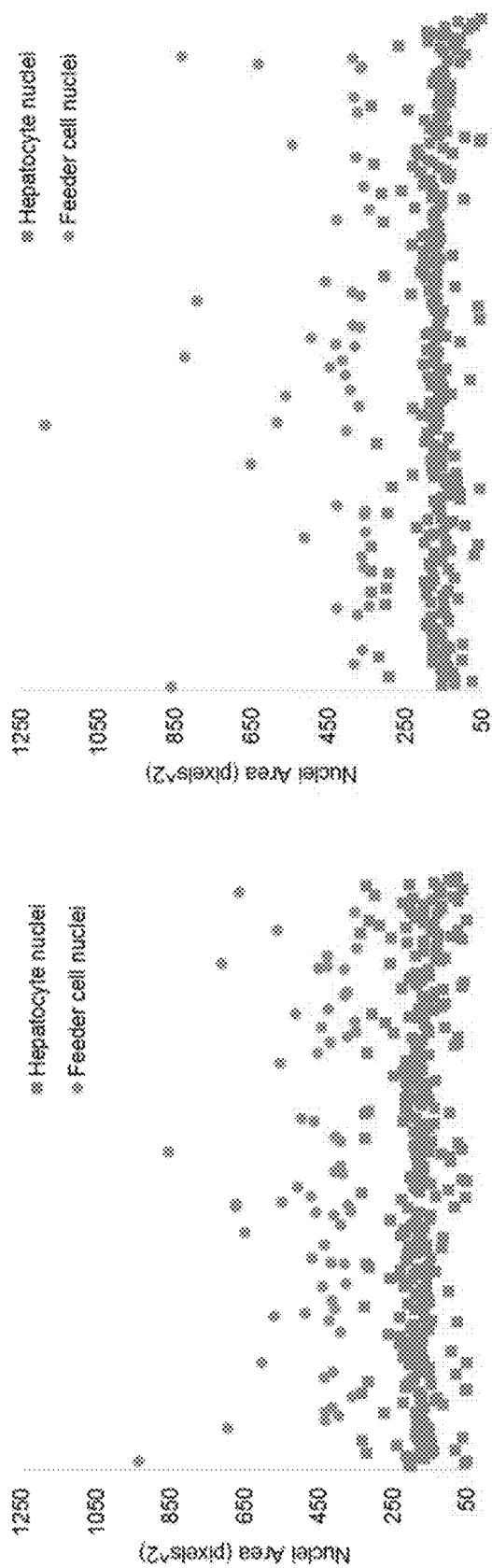
FIG. 26 shows geographical distribution of hepatocytes and feeder cells in co-culture. Size of cellular nuclei was measured on Image J software from the entire field of image (left) and hepatocyte cluster (right).

Plateable quality hepatocytes were assessed through analysis of the overall area and nuclei characteristics within the regions not occupied by hepatocyte clusters in comparison to the total cell field. Suspension quality hepatocytes were assessed by analyzing the regions occupied by clusters in comparison with the total cell culture area. The feeder cells and hepatocytes were differentiated by the sizes of their respective nuclei. Fibroblasts and endothelial cells have a larger average nuclear size than hepatocytes. An average nuclear size of the feeder cells was established by measuring the nuclear size of feeder cells alone in the co-culture. A threshold of the average feeder cell area plus one standard deviation was used to distinguish between hepatocytes and feeder cells. The threshold used was a hepatocyte nuclei area less than 345 pixels^2. All measurements were taken with ImageJ (FIG. 26).

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A product comprising plated human hepatocytes on a surface, wherein at least 70% of the plated hepatocytes are in one or more hepatocyte clusters on feeder cells, wherein the feeder cells are endothelial cells and fibroblasts and are attached to the surface.

2. The product of claim 1, wherein at least 90% of the plated hepatocytes in the one or more hepatocyte clusters are in direct hepatocyte-hepatocyte contact.

3. The product of claim 1, wherein the one or more hepatocyte clusters cover at least 50% of the surface.

4. The product of claim 1, further comprising a culture medium, wherein at least 90% of the plated hepatocytes remain on the surface for at least 7 days.

5. The product of claim 1, wherein the endothelial cells are not liver cells.

6. The product of claim 1, wherein the fibroblasts are not liver cells.

7. The product of claim 1, wherein the plated hepatocytes are obtained from a single donor, and wherein the donor has suffered from microsteatosis.

8. The product of claim 1, wherein the plated hepatocytes are obtained from a single donor, and wherein the donor has suffered from nonalcoholic steatohepatitis (NASH).

9. A method of preparing plated human hepatocytes, comprising (a) applying human hepatocytes to a surface in the presence of feeder cells, wherein the feeder cells are endothelial cells and fibroblasts, (b) co-culturing the applied hepatocytes with the feeder cells after step (a), and (c) forming one or more hepatocyte clusters by the co-cultured hepatocytes on the feeder cells, wherein the feeder cells are attached to the surface, wherein at least 85% of the co-cultured hepatocytes are in the one or more hepatocyte clusters, whereby plated human hepatocytes are prepared.

10. The method of claim 9, wherein the applied hepatocytes in step (a) have a platability of less than 60% on the surface in the absence of the feeder cells.

11. The method of claim 9, wherein the applied hepatocytes in step (a) have a platability of at least 85% on the surface in the absence of the feeder cells.

12. The method of claim 9, wherein at least 90% of the plated hepatocytes remain on the surface for at least 7 days.

13. The method of claim 9, wherein the feeder cells are attached to the surface in step (b).

14. The method of claim 9, wherein the method excludes addition of an extracellular matrix protein.

15. A method of preparing a hepatitis B virus (HBV) infected hepatocyte culture model, comprising (a) inoculating the plated hepatocytes in the product of claim 1 with hepatitis B virus (HBV), and (b) incubating the infected plated hepatocytes for at least 14 days, whereby the HBV infected hepatocyte culture model is prepared.

16. The product of claim 1, wherein the fibroblasts and endothelial cells have 0% to 10% interference in biological activity with the hepatocytes.

* * * * *